(12) United States Patent
Cales et al.

(10) Patent No.: US 9,585,613 B2
(45) Date of Patent: Mar. 7, 2017

(54) DIAGNOSIS OF LIVER FIBROSIS AND CIRRHOSIS

(75) Inventors: Paul Cales, Avrille (FR); Jérôme Boursier, Angers (FR)

(73) Assignees: UNIVERSITE D'ANGERS, Angers (FR); CENTRE HOSPITALIER UNIVERSITAIRE D'ANGERS, Angers (FR)

(*) Notice: Subject to any disclaimer, the term of this patent is extended or adjusted under 35 U.S.C. 154(b) by 369 days.

(21) Appl. No.: 13/203,397

(22) PCT Filed: Feb. 26, 2010

(86) PCT No.: PCT/EP2010/052506
§ 371 (c)(1),
(2), (4) Date: Aug. 25, 2011

(87) PCT Pub. No.: WO2010/097472
PCT Pub. Date: Sep. 2, 2010

(65) Prior Publication Data
US 2011/0306849 A1    Dec. 15, 2011

Related U.S. Application Data

(60) Provisional application No. 61/155,659, filed on Feb. 26, 2009.

(51) Int. Cl.
*A61B 5/00*      (2006.01)
*G06F 19/00*     (2011.01)
*A61B 8/08*      (2006.01)

(52) U.S. Cl.
CPC ............ *A61B 5/416* (2013.01); *A61B 5/4244* (2013.01); *G06F 19/345* (2013.01); *A61B 8/08* (2013.01); *A61B 8/485* (2013.01)

(58) Field of Classification Search
USPC ............................ 600/300–301; 436/86, 94
See application file for complete search history.

(56) References Cited

U.S. PATENT DOCUMENTS 6,631,330 B1 * 10/2003 Poynard .......................... 702/19
7,856,319 B2 * 12/2010 Poynard .......................... 702/19
(Continued)

FOREIGN PATENT DOCUMENTS

CN        1985259      6/2007
WO      03/073822      9/2003
(Continued)

OTHER PUBLICATIONS

Adams et al., "Hepascore: an accurate validated predictor of liver fibrosis in chronic hepatitis C infection," *Clin Chem*, 51:1867-1873, 2005.
(Continued)

*Primary Examiner* — William Thomson
*Assistant Examiner* — Bobby Soriano
(74) *Attorney, Agent, or Firm* — Norton Rose Fulbright US LLP

(57) ABSTRACT

This invention relates to method of diagnosing the presence and/or severity of a liver pathology and/or of monitoring the effectiveness of a curative treatment against a liver pathology in an individual, leading to a score, comprising the combination, of at least one blood test and of at least one data issued from a physical method of diagnosing liver fibrosis, said data being selected from the group consisting of medical imaging data and clinical measurements, said combination being performed through a mathematical function. This invention also relates to a method wherein the combination through a mathematical function, of at least one blood test and of at least one data issued from a physical method of diagnosing liver fibrosis, is performed at least twice and the at least two resulting scores are combined in an algorithm based on the diagnostic reliable intervals.

9 Claims, 5 Drawing Sheets

(56) References Cited

U.S. PATENT DOCUMENTS

Figure 1:
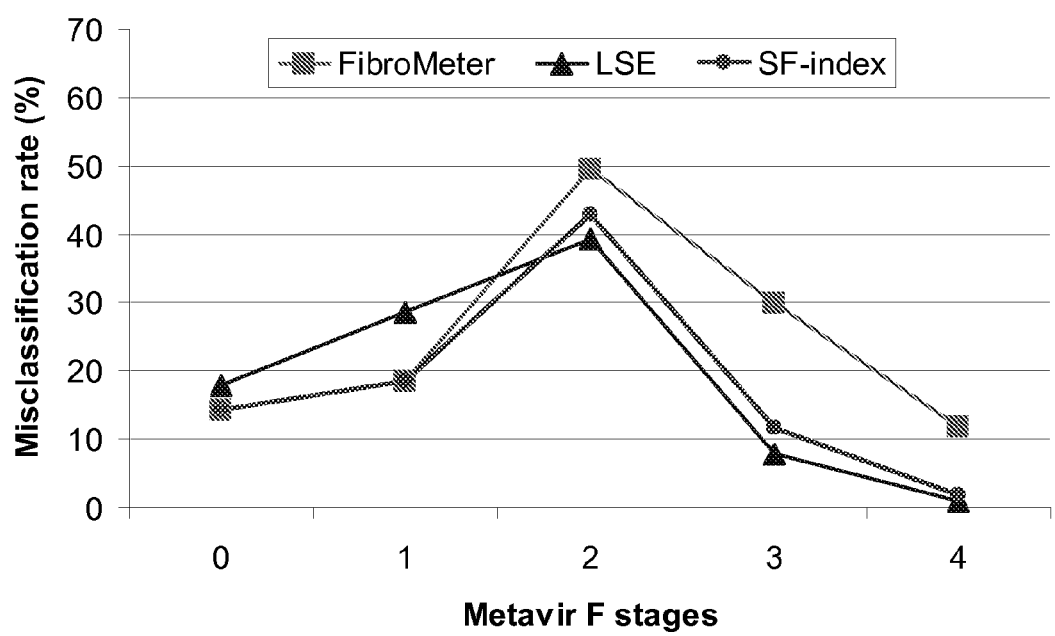

| | | | |
|---|---|---|---|
| 2003/0175686 A1 | 9/2003 | Rose et al. | 435/5 |
| 2004/0053242 A1 | 3/2004 | Volker et al. | 435/6.16 |
| 2006/0014294 A1* | 1/2006 | Contreras et al. | 436/86 |
| 2006/0052696 A1* | 3/2006 | Shiina | A61B 5/0048 600/437 |
| 2006/0253020 A1 | 11/2006 | Ehman et al. | 600/411 |
| 2007/0129633 A1 | 6/2007 | Lee et al. | 600/439 |
| 2007/0172907 A1* | 7/2007 | Volker | C12Q 1/6883 435/15 |
| 2007/0178442 A1* | 8/2007 | Wienhues-Thelen | G01N 33/6893 435/4 |
| 2007/0178443 A1* | 8/2007 | Wienhues-Thelen et al. | 435/4 |
| 2007/0225919 A1* | 9/2007 | Jeffrey et al. | 702/19 |
| 2008/0249408 A1* | 10/2008 | Palmeri et al. | 600/438 |
| 2009/0111132 A1* | 4/2009 | Poynard | 435/11 |
| 2009/0117591 A1* | 5/2009 | Corrales Izquierdo et al. | 435/7.4 |
| 2009/0143993 A1* | 6/2009 | Cales | 702/19 |
| 2010/0036273 A1* | 2/2010 | Ben-Oren | A61K 51/04 600/532 |
| 2010/0041069 A1* | 2/2010 | Lederkremer | 435/7.4 |
| 2010/0049029 A1* | 2/2010 | Li et al. | 600/410 |
| 2010/0241012 A1* | 9/2010 | Yin et al. | 600/485 |
| 2010/0303724 A1* | 12/2010 | Jandrot-Perrus . | C07K 14/70503 424/9.1 |
| 2011/0060210 A1* | 3/2011 | Ehman | 600/410 |
| 2011/0313276 A1* | 12/2011 | Cales et al. | 600/410 |

FOREIGN PATENT DOCUMENTS

| | | |
|---|---|---|
| WO | WO 03/073822 | 9/2003 |
| WO | 2005/116901 | 12/2005 |

OTHER PUBLICATIONS

Afdhal and Nunes, "Evaluation of liver fibrosis: a concise review," *Am J Gastroenterol*, 99:1160-1174, 2004.

Bossuyt et al., "The STARD statement for reporting studies of diagnostic accuracy: explanation and elaboration," *Clin Chem*, 49:7-18, 2003.

Bourliere et al., "Optimized stepwise combination algorithms of non-invasive liver fibrosis scores including Hepascore in hepatitis C virus patients," *Aliment Pharmacol Ther*, 28:458-467, 2008.

Bourliere et al., "Validation and comparison of indexes for fibrosis and cirrhosis prediction in chronic hepatitis C patients: proposal for a pragmatic approach classification without liver biopsy," *J Viral Hepat*, 13:659-670, 2006.

Boursier et al., "Improved diagnostic accuracy of blood tests for severe fibrosis and cirrhosis in chronic hepatitis C," *Eur J Gastroenterol Hepatol*, 21:28-38, 2009.

Boursier et al., "Learning curve and interobserver reproducibility evaluation of liver stiffness measurement by transient elastography," *Eur J. Gastroenterol Hepatol*, 20:693-701, 2008.

Boursier et al., "Reproducibility of liver stiffness measurement by ultrasonographic elastometry," *Clin Gastroenterol Hepatol*, 6:1263-1269, 2008.

Cales et al., "A novel panel of blood markers to assess the degree of liver fibrosis," *Hepatology*, 42:1373-1381, 2005.

Cales et al., "Comparison of blood tests for liver fibrosis specific or not to NAFLD", *J. Hepatol*, 50:165-173, 2009.

Cales et al., "Comparison of reproducibility of histology, blood tests and Fibroscan for liver fibrosis," *Hepatology*, 46:834A, 2007.

Cales et al., "Evaluating accuracy and increasing the reliable diagnosis rate of blood tests for liver fibrosis in chronic hepatitis C," *Liver Int*, 28:1352-1362, 2008.

Cales et al., "Evaluation and improvement of a reliable diagnosis of cirrhosis by blood tests," *Gastroenterol Clin Biol*, 32:1050-1060, 2008.

Cales et al., "Fibrometers: a family of blood tests for liver fibrosis," *Gastroenterologie Clinique et Biologique*, 32(6S1):40-51, 2008.

Cales et al., "Reproducibility of blood tests for liver fibrosis in clinical practice," *Clim Biochem*, 41:10-18, 2008.

Castera et al., "Prospective comparison of transient elastography, Fibrotest, APRI and liver biopsy for the assessment of fibrosis in chronic hepatitis C," *Gastroenterology*, 128:343-350, 2005.

Castera et al., "Prospective comparison of two algorithms combining non-invasive tests for staging of liver fibrosis in chronic hepatitis C," *Hepatology*, 46:320A, 2007.

Castera, "Use of elastometry (FibroScan) for the non-invasive staging of liver fibrosis," *Gastroenterol Clin Biol*, 31:524:530, 2007.

Croquet et al, "Prothrombin index is an indirect marker of severe liver fibrosis," *Eur J. Gastroenterol Hepatol*, 14:1133-1141, 2002.

DeLong et al., "Comparing the areas under two or more correlated receiver operating characteristic curves: a nonparametric approach," *Biometrics*, 44:837-845, 1988.

Fraquelli et al., "Reproducibility of transient elastography in the evaluation of liver fibrosis in patients with chronic liver disease," *Gut*, 56:968-973, 2007.

Friedrich-Rust et al., "Performance of transient elastography for the staging of liver fibrosis: a meta-analysis," *Gastroenterology*, 134:960-974, 2008.

Friedrich-Rust et al., "Real-Time elastography for noninvasive assessment of liver fibrosis in chronic viral hepatitis," *Am J Roentgenol*, 188:758-764, 2007.

Halfon et al, "Comparison of test performance profile for blood tests of liver fibrosis in chronic hepatitis C,"*J Hepatol*, 46:395-402, 2007.

Imbert-Bismut et al., "Biochemical markers of liver fibrosis in patients with hepatitis C virus infection: a prospective study," *Lancet*, 357:1068-1075, 2001.

International Search Report, issued in International Patent Application No. PCT/EP2010/052506, mailed on Jun. 10, 2010.

Lambert et al., "How to measure the diagnostic accuracy of non-invasive liver fibrosis indices: the area under the ROC curve revisited," *Clin Chem*, 54:1372-1378, 2008.

Lucidarme et al., "Factors of accuracy of transient elastography (Fibroscan) for the diagnosis of liver fibrosis in chronic hepatitis C," *Hepatology*, 49(4):1083-1089, 2009.

Nousbaum et al., "Clinical practice guidelines on the use of liver biopsy," *Gastroenterol Clin Biol*, 26:848-878, 2002.

Oberti et al., "Noninvasive diagnosis of hepatic fibrosis or cirrhosis," *Gastroenterology*, 113:1609-1616, 1997.

Obuchowski, "An ROC-type measure of diagnostic accuracy when the gold standard is continuous-scale," *Stat Med*, 25:481-493, 2006.

Patel et al., "Evaluation of a panel of non-invasive serum markers to differentiate mild from moderate to advanced liver fibrosis in chronic hepatitis C patients," *J Hepatol*, 41:935-942, 2004.

Poynard et al., "Standardization of ROC curve areas for diagnostic evaluation of liver fibrosis markers based on prevalence of fibrosis stages," *Clin Chem*, 53:1615-1622, 2007.

Rosenberg et al, "Serum markers detect the presence of liver fibrosis: a cohort study," *Gastroenterology*, 127:1704-1713, 2004.

Sandrin et al., "Transient elastography: a new noninvasive methods for assessment of hepatic fibrosis," *Ultrasound Med Biol*, 29:1705-1713, 2003.

Sebastiani and Alberti, "Non-invasive fibrosis biomarkers reduce but not substitute the need for liver biopsy," *World J Gastroenterol*, 12:3682-3694, 2006.

Sebastiani et al., "Large-scale multicenter comparison of three algorithms combining serum non-invasive markers for liver fibrosis in chronic hepatitis C,"*J Hepatol*, 48: S282, 2008.

Sebastiani et al., "Sequential algorithms combining non-invasive markers and biopsy for the assessment of liver fibrosis in chronic hepatitis B," *World J Gastroenterol*, 13:525-531, 2007.

Sebastiani et al., "Stepwise combination algorithms of non-invasive markers to diagnose significant fibrosis in chronic hepatitis C," *J. Hepatol.*, 44:686-693, 2006.

Sterling et al., "Development of a simple noninvasive index to predict significant fibrosis in patients with HIV/HCV coinfection," *Hepatology*, 43:1317-1325, 2006.

(56) References Cited

OTHER PUBLICATIONS

Wai et al., "A simple noninvasive index can predict both significant fibrosis and cirrhosis in patients with chronic hepatitis," *Hepatology*, 38:518-526, 2003.

Bourliere et al, Optimized stepwise combination algorithms of non-invasive liver fibrosis scores including Hepascore in hepatitis C virus patients, Alimentary Pharmacology & Therapeutics, 2008, 28(4): 458-467.

Calés et al, Accuracy of liver fibrosis classifications provided by non-invasive tests, 2010, Journal of Hepatology, 52 : S406.

Cales P, et al, A novel panel of blood markers to assess the degree of liver fibrosis, Hepatology 2005;42:1373-1381.

Cales P et al, Evaluating the accuracy and increasing the reliable diagnosis rate of blood tests for liver fibrosis in chronic hepatitis C, Liver Int 2008;28:1352-1362.

Croquet et al, Prothrombin index is an indirect marker of severe liver fibrosis, European Journal of Gastroenterology & Hepatology, 2002, 14(10): 1133-1141.

Ghany et al, Progression of fibrosis in chronic hepatitis C, Gastroenterology, 2003, 124(1): 97-104.

Halfon et al, Comparison of test performance profile for blood tests of liver fibrosis in chronic hepatitis C, Journal of Hepatology, 2007, 46(3): 395-402.

Halfon et al, Serum markers of non-invasive fibrosis in chronic hepatitis C virus infection, La revue de médecine interne, 2006, 27(10): 751-61.

Hubert JB, et al, Natural history of serum HIV-1 RNA levels in 330 patients with a known date of infection. The SEROCO Study Group, Aids 2000;14:123-131.

Leroy et al, Changes in histological lesions and serum fibrogenesis markers in chronic hepatitis C patients non-responders to interferon alpha, Journal of Hepatology, 2001, 35(1): 120-126.

Leroy et al, Prospective comparison of six non-invasive scores for the diagnosis of liver fibrosis in chronic hepatitis C, Journal of Hepatology, 2007, 46(5): 775-82.

Maor et al, Improving estimation of liver fibrosis using combination and newer noninvasive biomarker scoring systems in hepatitis C-infected haemophilia patients, Haemophilia, 2007, 13(6): 722-9.

Marcellin et al, Fibrosis and disease progression in hepatitis C, Hepatology 2002, 36(5)—supplement 1: S47-S56.

Meriden et al, Histologic predictors of fibrosis progression in liver allografts in patients with hepatitis C virus infection, Clinical gastroenterology and hepatology, 2010, 8(3): 289-296.

Michalak et al, Respective roles of porto-septal fibrosis and centrilobular fibrosis in alcoholic liver disease, Journal of Pathology, 2003, 201(1): 55-62.

Myers et al, Biochemical markers of fibrosis in patients with chronic hepatitis C: a comparison with prothrombin time, platelet count, and age-platelet index, Digestive diseases and Sciences, 2003, 48(1): 146-153.

Sebastiani et al, Sequential algorithms combining non-invasive markers and biopsy for the assessment of liver fibrosis in chronic hepatitis B, World journal of gastroenterology, 2007, 13(4): 525-531.

Arena U et al., "Acute viral hepatitis increases liver stiffness values measured by transient elastography," Hepatology, Feb. 2008; 47(2):380-384.

Barreiro P et al., "Predictors of liver fibrosis in HIV-infected patients with chronic hepatitis C virus (HCV) infection: assessment using transient elastometry and the role of HCV genotype 3," Clinical Infectious Diseases., Apr. 1, 2006; 42(7):1032-1039.

Foucher J et al., "Diagnosis of cirrhosis by transient elastography (FibroScan): a prospective study," Gut, Mar. 2006; 55(3):403-408.

Kawamoto M et al., "Assessment of liver fibrosis by a noninvasive method of transient elastography and biochemical markers," World Journal of Gastroenterology, Jul. 21, 2006; 12(27):4325-4330.

Nguyen-Khac et al., "Assessment of asymptomatic liver fibrosis in alcoholic patients using fibroscan: prospective comparison with seven non-invasive laboratory tests.," Alimentary Pharmacology & Therapeutics, Nov. 15, 2008; 28(10):1188-1198.

Posthouwer D, "Significant liver damage in patients with bleeding disorders and chronic hepatitis C: non-invasive assessment of liver fibrosis using transient elastography," Journal of Thrombosis and Haemostasis, Jan. 2007; 5(1):25-30.

Saito H et al., "Efficacy of non-invasive elastometry on staging of hepatic fibrosis," Hepatology Research, Jun. 2004; 29(2):97-103.

Sporea I et al., "Liver stiffness measurement by transient elastography in clinical practice," Journal of Gastrointestinal and Liver Diseases, Dec. 2008; 17(4):395-399.

\* cited by examiner

2a

2b

DIAGNOSIS OF LIVER FIBROSIS AND CIRRHOSIS

This application is a national phase application under 35 U.S.C. §371 of International Application No. PCT/EP2010/052506 filed 26 Feb. 2010, which claims priority to U.S. Provisional Application No. 61/155,659 filed 26 Feb. 2009. The entire text of each of the above-referenced disclosures is specifically incorporated herein by reference without disclaimer.

This invention relates to an improved diagnosis method of liver fibrosis or cirrhosis, through combination of at least one blood test and at least one physical method for diagnosing liver fibrosis, in an individual, especially in an individual suffering from a condition involving significant or severe fibrosis or cirrhosis. The method of the invention leads to scores called SF or C-index and optionally to combination thereof.

Liver biopsy is the historical means in order to diagnose liver disease in patients. However, since liver biopsy is invasive and expensive, non-invasive diagnosis of liver fibrosis has gained considerable attention over the last 10 years as an alternative to liver biopsy. The first generation of simple blood fibrosis tests combined common indirect blood markers into a simple ratio, like APRI (5) or more recently FIB-4 (6). The second generation of calculated tests combined indirect and/or direct fibrosis markers by logistic regression, like Fibrotest (7), ELF score (8), FibroMeter (9), Fibrospect (10), and Hepascore (11). For example, WO03073822 describes a non-invasive method for the diagnosis of liver disease and its severity, by measuring levels of specific variables, including biological variables and clinical variables, and combining said variables into mathematical functions to provide a score, often called "score of fibrosis". The method of WO03073822 is also useful for monitoring the efficacy of a treatment of a liver disease or condition.

A further non-invasive diagnosis method of liver fibrosis is to use physical methods, for example ultrasonographic elastometry (12) in order to collect data useful for the diagnostic of fibrosis, such as for example "Liver Stiffness Evaluation" (LSE). In a recent article entitled "Performance of Transcient Elastography for the Staging of Liver Fibrosis: A Meta Analysis" released in *Gastroenterology* 2008; 134: 960-974 Friedrich-Rust et al validated "Transcient Elastometry" for the staging of Liver Fibrosis.

Finally, blood fibrosis tests have been combined into sequential algorithms in order to increase the diagnostic accuracy and limit the rate of liver biopsy (13-16). These sequential algorithms are usually based on a stepwise diagnosis including blood tests as a first step, followed by liver biopsy for the remaining grey zone of indeterminate cases. However, clinical applicability of these multiple-step sequential algorithms is difficult. Moreover, liver biopsy is still required in 20 to 50% of patients.

The diagnostic target of the present invention can be:
 a fibrosis class:
  significant fibrosis, defined as Metavir stages≥2 or Ishak stages≥3
  severe fibrosis, defined as Metavir stages≥3 or Ishak stages≥4
  cirrhosis defined as Metavir stages=4 or Ishak stages≥5
 the amount of fibrosis, like the area of fibrosis expressed in surface of fibrotic tissue compared to the whole liver tissue, or the three-dimensional amount of fibrosis, expressed in volume of fibrotic tissue compared to the whole liver tissue,
 the quantitative architecture of fibrosis, reflected by the fractal dimension like that of Kolgomorov.

One skilled in the art addressing such diagnostic technical issues, knows that the identification of reliable methods for early and accurate diagnosis of liver fibrosis is an ongoing process, and that there is a important medical need for continuing to improve the diagnosis of liver fibrosis and to improve the monitoring of the treatment of a liver disease or condition. Moreover, due to price and invasiveness of biopsy, there is still a need to reduce liver biopsy requirement. The diagnostic methods are appreciated by their performance, i.e. their ability to correctly classify the tested individuals, as to their fibrosis development.

Up to now, one skilled in the art used to implement blood tests combining blood markers and clinical markers such as age, sex, etc. . . . on the one hand, and imagery means on the other hand. Both blood test and imaging means were deemed as having their own specific advantages and one skilled in the art used blood tests or imaging means, depending on the Metavir stage of the patient.

The Applicant surprisingly realized that combining scores from blood tests and data issued from imaging means, resulted in a score having an incredibly high diagnostic performance (accuracy). When performing the present invention, the Applicant compared for the first time the diagnostic accuracy of imaging data, such as for example liver stiffness evaluation, and 5 blood tests, and compared their accuracy to the accuracy of their synchronous combination, either in a large population of patients with various causes of liver diseases or conditions (see example 2) or in an homogeneous population in terms of cause, such as for example patients suffering from chronic hepatitis C (see example 1).

At the time where the Applicant conceived the invention, one skilled in the art had no information whether or not the combination of scores issued from blood tests and of data issued from imaging means was of interest. The statistical evaluation, e.g. trough differences between the AUROCs (Area Under the Receiver Operating Characteristic), i.e. the main diagnostic information ever used combining sensitivity and specificity, of this combination had not been performed yet at the date of invention.

As an example of data of interest issued from imaging means, is the Liver Stiffness Evaluation (LSE). LSE was known for having a good accuracy for the diagnosis of cirrhosis but reproducibility of LSE was poor in early fibrosis stages. For this reason, LSE was mainly used for the diagnostic of cirrhosis.

For early fibrosis stages, blood tests have shown higher reproducibility and accuracy than LSE.

Surprisingly, the Applicant has found that the combination of diagnostic information from blood tests and data from imaging means, especially but not exclusively Fibroscan™ or ARFI (Acoustic Radiation Force Impulse imaging) data, such as for example LSE data, provided several advantages and unexpected accurate results for the diagnosis of liver fibrosis, from significant fibrosis to severe fibrosis and cirrhosis.

The Applicant has also set up a first algorithm, called Angers SF-algorithm, combining scores from blood test and imaging data, preferably Fibroscan data, appeared to be, at the date of priority of the present application, the best solution among known alternatives to the Applicant, such as high correct classification and low liver biopsy requirement, reflected by a low liver biopsy/accuracy ratio.

The present invention thus relates to a non-invasive method leading to a score obtained by a mathematical function, such as for example a binary logistic regression, combining blood test score and imaging, preferably Fibroscan, data for assessing, with a high accuracy, the presence or the severity of fibrosis in an individual.

The synchronous combination set forth in the invention results in the accumulation of blood tests and imaging means advantages, in the substraction of their drawbacks, thereby significantly increasing the single diagnostic accuracy for liver fibrosis.

1. In an embodiment, the method of the invention includes repeting several times, at least twice, the method, in order to obtain at least two scores. In this embodiment, the method of the invention may also include, in a further step, the combination of at least two scores as described hereabove (i.e. two scores obtained by a mathematical function, such as for example a binary logistic regression, combining blood test score and imaging, preferably Fibroscan, data), said combination being implemented in an algorithm based on the diagnostic reliable intervals (see for example table 5 of example 1). Carrying out this further step leads to three new scores/classifications called F≥2 index, F≥3 index, F4 index) for the non-invasive diagnosis of fibrosis. Implementing this further step is of high industrial interest, and results in extended accuracy. Thus, the invention also relates to a method wherein the combination through a mathematical function, of at least one blood test and of at least one data issued from a physical method of diagnosing liver fibrosis, is performed at least twice and the at least two resulting scores are combined in an algorithm based on the diagnostic reliable intervals.

The method of the invention improves the diagnostic accuracy and markedly reduces the biopsy requirement in algorithms.

This invention therefore relates to a method of diagnosing the presence and/or severity of a liver pathology and/or of monitoring the effectiveness of a curative treatment against a liver pathology in an individual, comprising the combination, of at least one blood test and at least one data issued from a physical method of diagnosing liver fibrosis selected from the group consisting of medical imaging data, including ultrasonographic elastometry (like Fibroscan™ or ARFI (Acoustic Radiation Force Impulse imaging)) data, and clinical measurements said combination being performed through a mathematical function. According to a first embodiment, the medical imaging data are LSE data. According to another embodiment, the clinical measurements, are measurements of spleen, especially length, as known by one skilled in the art to be interesting data for diagnosing fibrosis.

The mathematical function is known to one skilled in the art. The mathematical function preferably is a binary logistic regression.

More specifically, the method of the invention includes:
a) performing, from a blood sample of an individual, a score selected from the group consisting of APRI, FIB-4, Hepascore, Fibrotest™, and FibroMeter,
b) performing a physical method of diagnosing liver fibrosis in order to collect data related to fibrosis, and
c) combining the score and the data issued from physical method in a mathematical function, preferably a binary logistic regression, thus resulting in a new score for the diagnosis of the presence and/or severity of a liver pathology and/or of monitoring the effectiveness of a curative treatment against a liver pathology in an individual.

In a preferred embodiment, the combination is a synchronous combination. Synchronous combination is a one-step combination of data of step a) and data of step b) into a new score usually by binary logistic regression.

Performance of synchronous combination is carried out as follows: the results of the blood test and the data from physical method, preferably from Fibroscan™ or ARFI (Acoustic Radiation Force Impulse imaging), such as for example LSE data, are recorded in a first step. Then, their values are computerized to obtain the combined score.

The Applicant noticed that, unexpectedly, the score resulting from the implementation of the method of the invention, attesting the presence or the severity of a liver disease or condition, preferably resulting from the synchronous combination of a blood test and data from a physical method, preferably LSE data, preferably obtained through ultrasonographic elastometry, had an improved accuracy and, consequently, decreased the biopsy requirement in sequential algorithms (for diagnosis of significant fibrosis: biopsy requirement≈20%, for diagnosis of cirrhosis: biopsy requirement≈10%). According to the invention, the accuracy of the method of the invention is higher than 75%, preferably 80 to 99%, more preferably 85 to 95%, even more preferably around 90%. The accuracy means the number of patients correctly classified.

Preferably, the liver disease or condition is significant porto-septal fibrosis, severe porto-septal fibrosis, centrolobular fibrosis, cirrhosis, persinusoidal fibrosis, the fibrosis being from alcoholic or non-alcoholic origin. According to an embodiment, the individual is a patient with chronic Hepatitis C.

According to one embodiment of the invention, the blood test, is a score selected from the group consisting of APRI, FIB-4, Hepascore, Fibrotest™, and FibroMeter™. FibroMeter™ is preferred.

APRI is a blood test based on platelet and AST.

FIB-4 is a blood test based on platelet ASAT, ALT and age.

HEPASCORE is a blood test based on hyaluronic acid, bilirubin alpha2-macroglobulin, GGT, age and sex.

FIBROTEST™ is a blood test based on alpha2-macroglobulin, haptoglobin, apolipoprotein A1, total bilirubin, GGT, age and sex.

FIBROMETER™ is a family of blood tests the content of which depends on the cause of chronic liver disease and the diagnostic target with details in the following table:

| FibroMeter | Age | Sex | A2M | AH | PI | PLT | AST | Urea | GOT | Bili | ALT | Fer | Glu |
|---|---|---|---|---|---|---|---|---|---|---|---|---|---|
| F virus | x | x | x | x | x | x | X | x | | | | | |
| AOF virus | | | x | x | | x | | | x | x | x | | |
| F alcohol | x | | x | x | x | | | | | | | | |
| AOF alcohol | | | x | x | x | x | | | | | | | |
| F NAFLD | x | | | | | x | X | | | x | x | X | x | X |

A2M: alpha2-macroglobulin, HA: hyaluronic acid, PI: prothrombin index, PLT; platelets, Bili: bilirubin, Fer: ferritin, Glu: glucose; F: fibrosis score (Metavir), AOF: area of fibrosis, NAFLD: non alcoholic fatty liver disease Preferably, the physical method is selected from the group consisting of ultrasonography, especially Doppler-ultrasonography and elastometry ultrasonography and velocimetry ultrasonography, IRM, and MNR, especially MNR elastometry or velocimetry. Preferably, the data are LSE data. According to a preferred embodiment of the invention, the data are issued from a Fibroscan.

According to a preferred embodiment, the mathematical logistic regression function is the following:

$$score = a_0 + a_1 x_1 + a_2 x_2 + \ldots$$

wherein $a_i$ coefficients are constants and $x_i$ are independent variables.

This score corresponds to the p logit wherein p is the probability of presence of a significant or severe fibrosis, or of cirrhosis.

p is calculated as follows:

$$p = \exp(a_0 + a_1 x_1 + a_2 x_2 + \ldots)/(1 + \exp(a_0 + a_1 x_1 + a_2 x_2 + \ldots))$$

or $$p = 1/(1 + \exp(-a_0 - a_1 x_1 - a_2 x_2 - \ldots))$$

wherein $a_i$ and $x_i$ correspond to those of the score formula.

The presence of a lesion (for example significant fibrosis) is determined by a probability p higher than a diagnostic threshold generally equal to 0, 5 or equal to maximal Youden index (Se+Spe−1) or equal to maximal diagnostic performance (unless otherwise specified).

According to one embodiment of the invention, for significant fibrosis, coefficients that may be used in the binary regression of the method of the invention are the following: 3.9066 FM+0.1870 FS−2.8345, Where FM: FibroMeter value, FS: Fibroscan value.

According to another embodiment of the invention, for cirrhosis, coefficients that may be used in the binary regression of the method of the invention are the following: 3.6128 FM+0.1484 FS−6.4999

According to yet another embodiment of the invention, for severe fibrosis, coefficients that may be used in the binary regression of the method of the invention are the following: 3.3135 FM+0.1377 FS−4.2485.
Where FM: FibroMeter value, FS: Fibroscan value.

Scores of binary logistic regression: beta coefficients with 95% confidence intervals specifically observed in chronic viral hepatitis C, may be for example:

| Diagnostic target | FibroMeter | Fibroscan | Constant |
|---|---|---|---|
| Significant fibrosis (Metavir ≥ F2) | 3.90657157 (2.73122696; 5.08191618) | 0.18702583 (0.08912122; 0.28493045) | −2.83445806 (−3.68641133; −1.98250480) |
| Severe fibrosis (Metavir ≥ F3) | 3.31347460 (2.09369314; 4.53325606) | 0.13767514 (0.08253199; 0.19281830) | 4.24854774 (−5.18908296; −3.30801253) |
| Cirrhosis (Metavir F4) | 3.61284547 (1.49920710; 5.72648384) | 0.14837243 (0.09607115; 0.20067372) | −6.49993316 (−8.28162434; −4.71824198) | wherein
FM = FibroMeter ™
FS = Fibroscan ™

According to a preferred embodiment of the invention, the blood score is the FibroMeter score and the physical method data are LSE data through ultrasonographic elastometry. In all populations tested, the FibroMeter was always identified as the first independent predictor of significant fibrosis despite a slightly lower AUROC than LSE. Indeed, the FibroMeter provided the highest diagnostic accuracy in logistic regression. In addition, the FibroMeter might be the most accurate and robust among common blood tests (18). Among the various evaluations in the Applicant's study, the synchronous combination of FibroMeter and LSE was the most accurate for the diagnosis of significant fibrosis as well as for cirrhosis.

Advantageously, the presence or severity of liver disease or condition is diagnosed in two steps, first step being the FibroMeter blood test and second step being collecting data from a physical method, preferably LSE data, and wherein the combination of Fibrometer blood test and said data is performed through logistic regression.

According to the method of the invention, the liver biopsy/accuracy ratio may range from 0.10 for cirrhosis to 0.22 for clinically significant fibrosis; whereas this ratio ranges from 0.25 to 0.51 in classical algorithms without synchronous combination.

According to one embodiment, the method of the invention leads to a significant fibrosis score, called significant fibrosis-index (SF-index). This score was set up by using results from experimentations in a group of patients with both blood tests (preferably FibroMeter) and imaging data (preferably LSE data).

According to another embodiment of the invention, the method of the invention leads to a cirrhosis score, called C-index implementing the method of the invention, for the diagnosis of patients with cirrhosis.

Regarding the gain in accuracy provided by the method of the invention, the Applicant noticed that the method of the invention provided a significantly higher AUROC than the blood test or physical data, for example LSE, alone, especially for the diagnosis of significant fibrosis, and a gain in predictive values for cirrhosis (see for example Table 4 of Example 2).

Regarding the SF-index, it inherited the lowest misclassification rate provided by each single test in each fibrosis stage: the blood test in F0/1 stages, and LSE in F≥2 stages (see for example FIG. 1). Moreover, the SF-index resolved 66% of discordant cases between the blood test and LSE (see for example Table 5 of Example 2). Finally, SF-index significantly increased the rate of patients included in the interval of ≥90% predictive values (see for example Table 6 of Example 2). Therefore, SF-index induced a highly significant lower rate of Liver Biopsy than the blood test or LSE in sequential algorithm. Moreover, the three simple intervals of reliable diagnosis determined by SF-index (F0/1, F1±1, and F≥2) provided a non-invasive diagnosis in 100% of the population with 90.6% accuracy without liver biopsy requirement (see for example FIG. 3a).

Regarding the C-index, although it afforded no apparent significant gain in accuracy for cirrhosis diagnosis compared to LSE alone (see for example Table 3, 4 of Example 2), it did provide two advantages: 1) it resolved 68.4% of discordant cases between LSE and the blood test (see for example Table 5 of Example 2), and 2) the patient rate with ≥90% predictive values was significantly higher than with LSE or blood test alone (see for example Table 6 of Example 2), thus resulting in a very low rate of Liver Biopsy required in the algorithm (9%). Finally, the C-index allowed for a non-invasive diagnosis of cirrhosis in 100% of patients, with 90.3% accuracy, by considering three intervals of reliable individual diagnosis: no cirrhosis, F≥2, and cirrhosis, without liver biopsy requirement.

Regarding sequential algorithms, as demonstrated in a recent preliminary study (34), the Applicant showed that the Padova algorithm had a significantly higher diagnostic accuracy for significant fibrosis than the Bordeaux and Angers algorithms. However, this accuracy was mainly due to the high rate of required Liver Biopsy. In fact, to evaluate the clinical interest of an algorithm, the rates of required Liver Biopsy and of correctly classified patients among those not requiring Liver Biopsy are more appropriate descriptors than overall diagnostic accuracy. In that respect, the Angers algorithm provided the best solution between high diagnostic accuracy (91.9%) and the lowest rate of required Liver Biopsy (20.2%). Finally, it should be noticed that a part of apparently misclassified patients provided by an algorithm are in fact attributable to the misclassification of Liver Biopsy used as the reference (sampling error and observer variability).

In the work performed to reduce to practice the present invention, accuracies for the diagnosis of significant fibrosis or cirrhosis of the Bordeaux and Padova algorithms were similar to those previously published (16, 34, 35). Thus, the Applicant provides herein an independent external validation of these algorithms that were the previous reference in terms of algorithms. Interestingly, accuracies of the three algorithms were not significantly different between patients with chronic viral hepatitis and those with other cause of CLD, except for cirrhosis with the Angers C-algorithm. Because the Bordeaux and Padova algorithms were elaborated in chronic viral C hepatitis, the present invention states that these sequential algorithms can also be extended to other causes of CLD.

Thus, the method of the invention significantly increases the diagnostic accuracy of tests for significant fibrosis, and increases the reliability of individual diagnosis via predictive values for significant fibrosis and cirrhosis. The combination resolves discordant results between non-invasive tests and reduces non-concordant results with liver biopsy (LB). It also decreases the LB requirement in the traditional diagnosis of significant fibrosis or cirrhosis when they are the unique binary diagnostic targets. Also, the new method of reliable individual diagnosis, which adds an intermediate diagnostic target to the previous binary diagnostic target, suppresses or considerably diminishes any LB requirement. Finally, a simple sequential algorithm, including the synchronous blood test score+imaging data combination, provided high diagnostic accuracy while lowering LB requirement, notably to less than 10% for cirrhosis diagnosis.

According to an embodiment of the invention, the method of the invention may also include, in a further step, the combination of a SF-index and a C-index in an algorithm based on the diagnostic reliable intervals (see for example table 5 of example 1).

The invention will be better understood in view of the following examples, which are read with consideration of the figures:

FIGS. 1 to 4 are to be read with regard to example 2. FIG. 5 is to be read with regard to Example 1.

FIG. 1: Misclassification rate (%) for significant fibrosis of FibroMeter, liver stiffness evaluation (LSE), and their synchronous combination (SF-index) as a function of Metavir fibrosis stages. Diagnostic cut-offs used for significant fibrosis were, according to the highest Youden index: FibroMeter: 0.538, LSE: 6.9 kiloPascals, and SF-index: 0.753.

Figure 2:
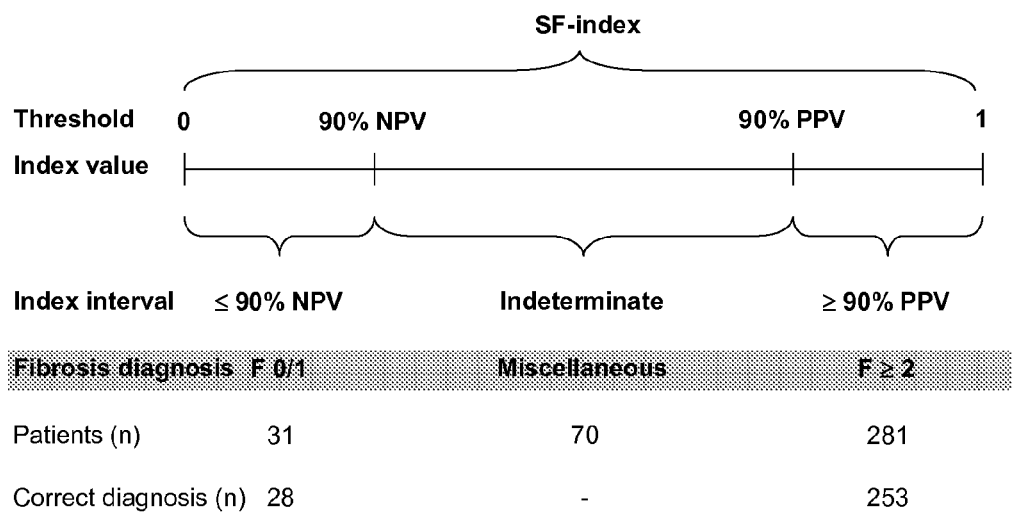
Figure 2:
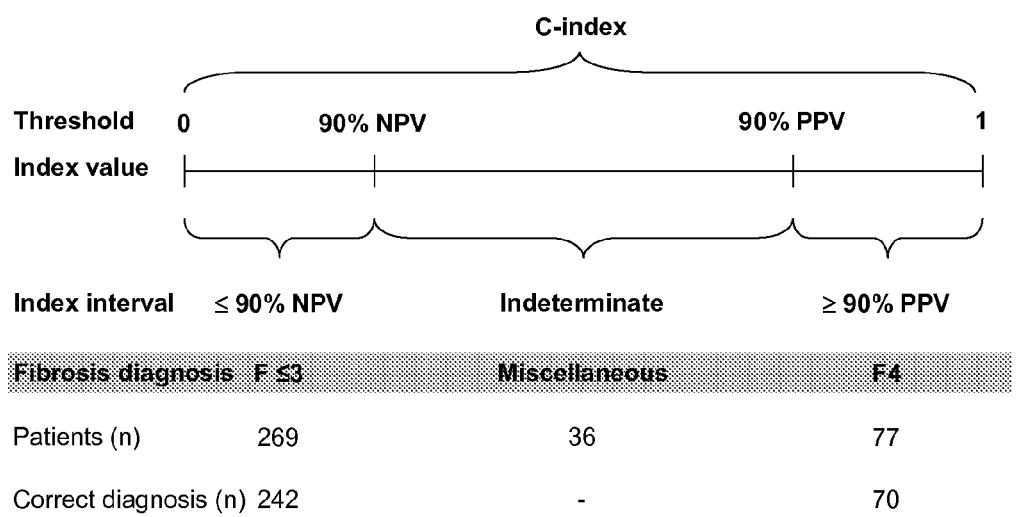

FIG. 2: Sequential algorithms for the diagnosis of significant fibrosis (Angers SF-algorithm, panel 2a) or cirrhosis (Angers C-algorithm, panel 2b). A specific score combining FibroMeter and LSE is initially used (SF-index for significant fibrosis or C-index for cirrhosis), and liver biopsy is subsequently required in case of indeterminate diagnosis.

Figure 3:
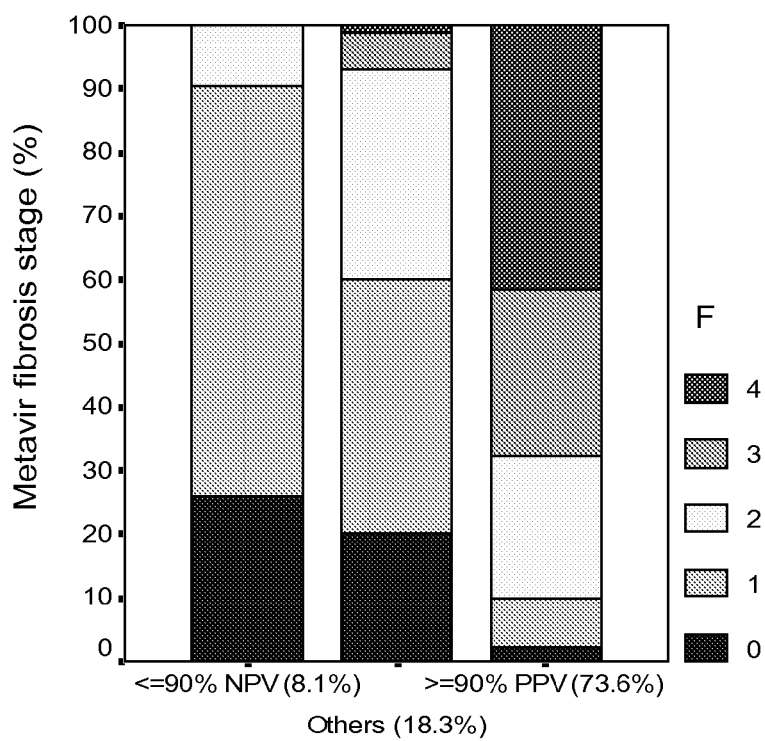
Figure 3:
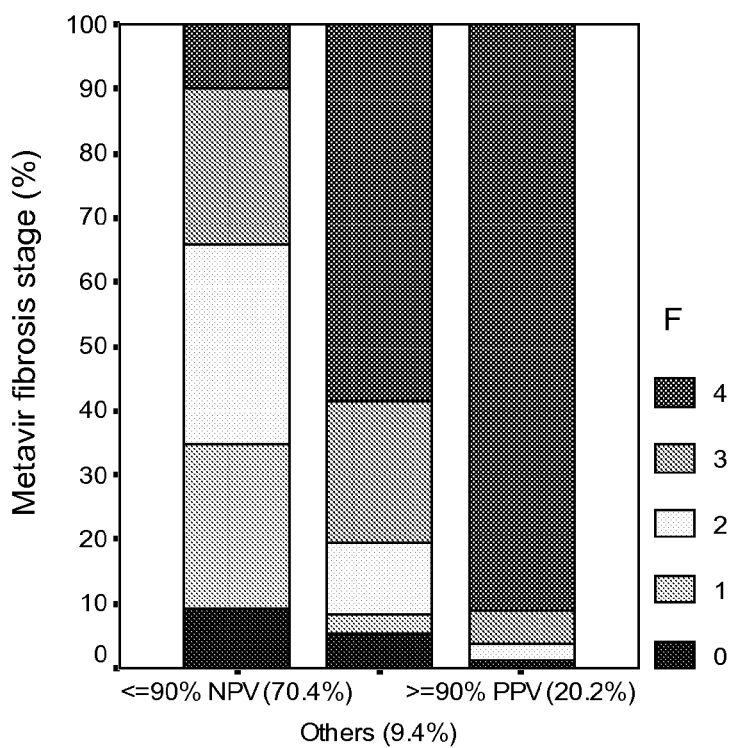

FIG. 3: Reliable diagnosis intervals for significant fibrosis (panel 3a) or cirrhosis (panel 3b): proportion of Metavir fibrosis (F) stages, according to liver biopsy, on Y axis as a function of intervals determined by thresholds of 90% negative (NPV) and positive (PPV) predictive values of SF-index (3a) or C-index (3b) on X axis. Rates of patients (%) included in the intervals of reliable diagnosis are depicted in parentheses on X axis.

Figure 4:
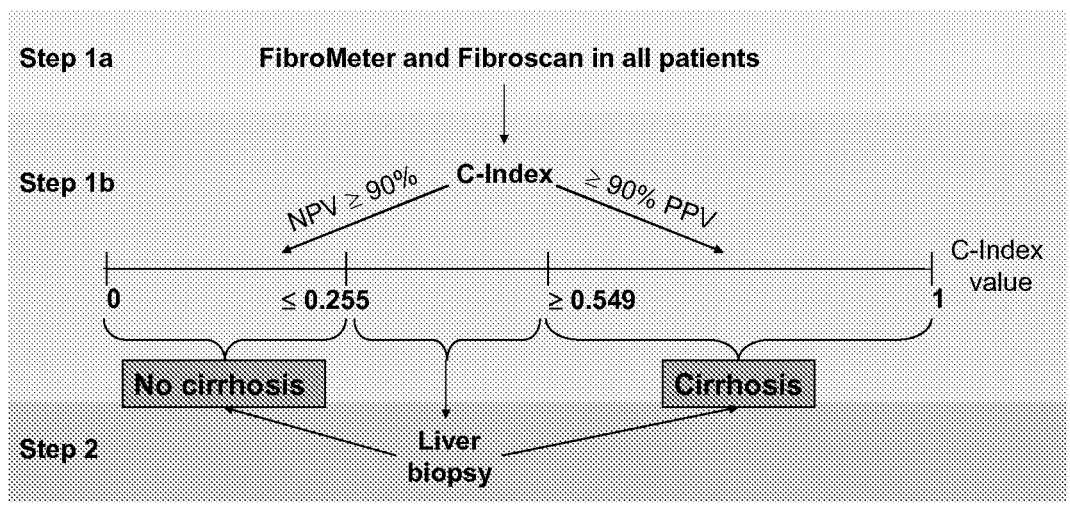
Figure 5:
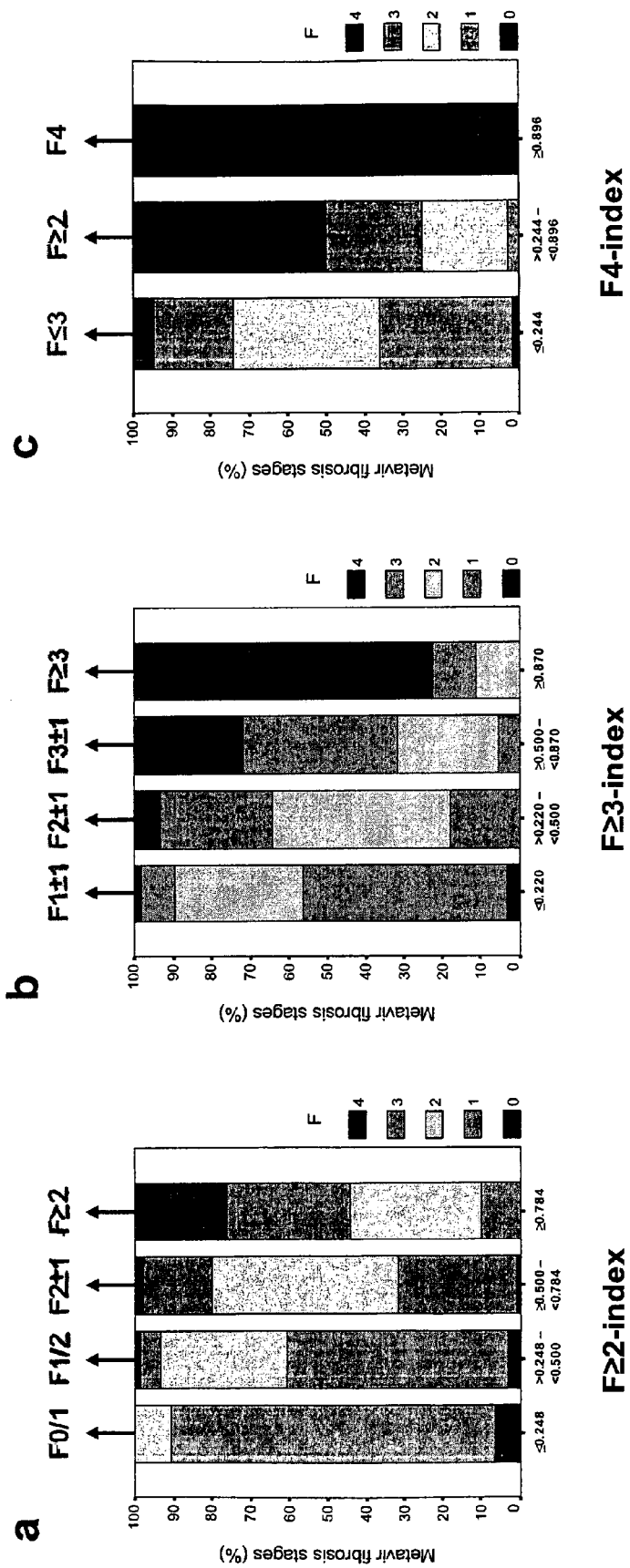

FIG. 4: Practical algorithm for the diagnosis of cirrhosis (Angers C-algorithm). A score combining FibroMeter and Fibroscan values (C-index) is calculated in a first step. According to the present study, in the first non-invasive step, cirrhosis was excluded in 70.4% of patients and affirmed in 20.2%. Liver biopsy was required in a second step in only 9.4% of patients.

FIG. 5: Intervals of reliable diagnosis of F≥2-, F≥3- and F4-indexes. Panel 1a: proportion of Metavir fibrosis stages (F) according to the statistical diagnostic cut-off (0.500) and the thresholds of 90% negative and positive predictive values for significant fibrosis with F≥2-index. Panel 1b: proportion of Metavir fibrosis stages (F) according to the statistical diagnostic cut-off (0.500) and the thresholds of 90% negative and positive predictive values for severe fibrosis with F≥3-index. Panel 1b: proportion of Metavir fibrosis stages (F) according to the thresholds of 95% predictive values for cirrhosis with F4-index.

EXAMPLES

The following examples may be read, when appropriate, with references to the figures, and shall not be considered as limiting in any way the scope of this invention.

Example 1

Blood fibrosis tests and liver stiffness measured by ultrasonographic elastometry like Fibroscan™ are well correlated with the histological stages of fibrosis. In this study, we aimed to improve non-invasive diagnosis of liver fibrosis stages via a novel combination of blood tests and Fibroscan. Methods: 349 patients with chronic hepatitis C across three centres were included in the study. For each patient, a liver biopsy and the following fibrosis tests were done: Fibroscan (FS), Fibrotest, FibroMeter (FM, for significant fibrosis or cirrhosis), Hepascore, Fib4, and APRI. Reference for liver fibrosis was Metavir F staging. Fibrosis tests independently associated with significant fibrosis (F≥2) or cirrhosis (F4) were identified by stepwise binary logistic regression repeated on 1000 bootstrap samples of 349 patients.
Results: Prevalences of diagnostic targets were, significant fibrosis: 67.9%, cirrhosis: 11.8%. Multivariate analyses on the 1000 bootstrap samples indicated that FM and FS were the tests most frequently associated with significant fibrosis or cirrhosis. We thus implemented 2 new scores combining FS and FM by using binary logistic regression: F2-score for the diagnosis of significant fibrosis and F4-score for cirrhosis. F2-score provided reliable diagnosis of significant fibrosis, with predictive values≥90%, in 55.6% of patients. F4-score provided reliable diagnosis of cirrhosis, with predictive values≥95%, in 89.1% of patients. An algorithm combining F2-score and F4-score, as a function of their interval of highest diagnostic accuracy, produced a new diagnostic classification (% of patients): F0/1 (9.5%), F1/2 (17.2%), F2±1 (27.2%), F2/3 (33.2%), F3±1 (10.9%), and F4 (2.0%). According to liver biopsy results, this new classification provided 88.0% diagnostic accuracy, outperforming FM (67.6%, $p<10^{-3}$), FS (55.3%, $p<10^{-3}$) and Fibrotest (33.2%, $p<10^{-3}$) classifications. Furthermore, diagnostic accuracy of the new classification did not significantly differ over the 3 centres (92.9%, 85.7%, and 86.3%, p=0.20) or between patients with biopsies < or ≥25 mm (respectively: 87.2% versus 88.5%, p=0.72).

Conclusions: The non-invasive diagnosis of liver fibrosis in patients with chronic hepatitis C is improved by a combination of FibroMeter and Fibroscan. A new classification using the two scores derived from the test combination is much more accurate than single fibrosis tests and provides a non-invasive diagnosis in 100% of patients with 88% accuracy without any liver biopsy.

Patients

The exploratory set included 349 patients. 132 patients from the 512 of the Fibrostar study were already included in the exploratory set. We thus removed these patients from the validation set which finally included 380 patients. The characteristics of both exploratory and validation sets are detailed in the Table 1 of Example 1. Among the 2 groups, 93.5% of liver biopsy were considered as reliable.

Implementation of the New Classifications (Exploratory Set)

New Scores Combining Blood Fibrosis Tests and LSE

Significant fibrosis—The fibrosis tests most frequently selected by the stepwise binary logistic regression repeated on the 1000 bootstrap samples for the diagnosis of significant fibrosis were LSE and FibroMeter (Table 2 of Example 1). F≥2-index was implemented by including these 2 fibrosis tests as independent variables in a binary logistic regression performed in the whole population of the exploratory set. The regression score of F≥2-index, specifically designed for the diagnosis of significant fibrosis, was: 3.9066 FibroMeter+0.1870 LSE result−2.8345. F≥2-index had a significantly higher AUROC than FibroMeter and LSE (Table 3 of Example 1).

Severe fibrosis—The fibrosis tests most frequently selected by the 1000 bootstrap multivariate analyses were LSE and FibroMeter (Table 2 of Example 1). The regression score of F≥3-index including these 2 fibrosis tests and specifically designed for the diagnosis of severe fibrosis was: 3.3135 FibroMeter+0.1377 LSE result−4.2485. F≥3-index had a higher AUROC than FM and LSE, but the difference was significant only with FibroMeter (Table 3 of Example 1).

Cirrhosis—The fibrosis tests most frequently selected by the 1000 bootstrap multivariate analyses were also LSE and FibroMeter (Table 2 of Example 1). The regression score of F4-index including these 2 fibrosis tests and specifically designed for the diagnosis of cirrhosis was: 3.6128 FibroMeter+0.1484 LSE result−6.4999. F4-index had a higher AUROC than FM and LSE, but the difference was significant only with FibroMeter (Table 3 of Example 1).

Intervals of Reliable Diagnosis

Significant fibrosis—F≥2-index included 32 (9.2%) patient in the ≥90% negative predictive value (NVP) interval and 161 (46.1%) patients in the ≥90% positive predictive value (PPV) interval (Table 4 of Example 1). Thus, F≥2-index allowed a reliable diagnosis of significant fibrosis with ≥90% accuracy in 55.3% of patients, versus 33.8% with LSE ($p<10^{-3}$) and 55.6 with FibroMeter (p=1.00). The indeterminate interval between F≥2-index values>0.248 and <0.784 was divided into two new intervals according to the statistical cut-off of 0.500. 90.2% of the patients included in the lower interval (>0.248-<0.500) had F1/2 stages according to liver biopsy results, and 96.8% of patients included in the higher interval (≥0.500-<0.784) had F1/2/3 stages (FIG. 1a). Finally, F≥2-index provided 4 IRD: F0/1, F1/2, F2±1, and F≥2. By using these intervals, 92.0% of patients were well classified without any liver biopsy performed (FIG. 1a). FibroMeter provided the same 4 IRD which well classified 90.3% of patients (p=0.263 vs F≥2-index).

Severe fibrosis—F≥3-index included 174 (49.9%) patients in the intervals of ≥90% predictive values for severe fibrosis (Table 4 of Example 1), versus 41.8% with FibroMeter ($p<10^{-3}$) and 46.4% with LSE (p=0.235). By dividing the intermediate interval of F≥3-index according to the statistical cut-off of 0.500, F≥3-index provided 4 IRD (F≤2, F2±1, F≥2, F≥3; FIG. 1b) which well classified 91.7% of patients without any liver biopsy performed. By dividing its intermediate interval with the cut-off corresponding to the highest Youden index (9.2 kPa), LSE provided the same 4 IRD which well classified 91.1% of patients (p=0.860 vs F≥3-index).

Cirrhosis—F4-index included 313 (89.7%) patients in the intervals of ≥95% predictive values for cirrhosis (Table 4 of Example 1), versus 65.9% with FibroMeter ($p<10^{-3}$) and 87.4% with LSE (p=0.096). Dividing the intermediate interval according to the cut-off 0.500 did not allow for distinguish two different groups. Finally, F4-index provided 3 IRD (F≤3, F≥2, and F4) which well classified 95.1% of patients (FIG. 1c).

New Classifications

The first classification (classification A) was derived from both F≥2- and F≥3-indexes used with their IRD (Table 5 of Example 1). Classification A included 6 classes: F0/1, F1/2, F2±1, F2/3, F≥2, and F≥3. It provided 86.2% diagnostic accuracy in the exploratory set. The second classification (classification B) was derived from the IRD of F≥2- and F4 indexes (Table 5 of Example 1). Classification B included 6 classes (F0/1, F1/2, F2±1, F2/3, F≥2, F4) and provided 88.3% diagnostic accuracy (p=0.143 vs classification A). The third classification (classification C) was derived from the IRD for significant fibrosis of FibroMeter, and those for severe fibrosis of LSE (Table 5 of Example 1). Results of FibroMeter and LSE RDI were discordant in 2 patients which had thus undetermined diagnosis (Table 5 of Example 1). Classification C finally included 8 classes (F0/1, F1, F1/2, F2, F2±1, F2/3, F≥2, F≥3) and provided 84.0% diagnostic accuracy (p=0.229 vs classification A).

Validation of the Classifications (Validation Set)

Diagnostic accuracy of fibrosis tests classifications—The rates of well classified patients by the new classifications A and B were not significantly different in the validation set (respectively: 84.2% vs 82.4%, p=0.149), but were significantly higher than those of FibroMeter, LSE and Fibrotest (Table 6 of Example 1). One patient had undetermined diagnosis with the classification C that provided 70.3% diagnostic accuracy. Among already published classifications, FibroMeter provided the highest diagnostic accuracy (69.7%, p<0.029 vs LSE and Fibrotest), and Fibrotest the lower ($p<10^{-3}$ vs others). Finally, according to their diagnostic accuracies in the validation set, the classifications were ordered as follow: A, B>C>FibroMeter>LSE>Fibrotest (Table 6 of Example 1).

Influencing factors—In the whole study population, we performed a stepwise binary logistic regression including age, sex, biopsy length, Metavir F, and IQR/median as independent variables. Misclassification by classification A was independently associated only with the ratio IQR/median. In the validation set, classification A provided 88.2% diagnostic accuracy in patients with IQR/median<0.21 versus 70.1% in patients with IQR/median≥0.21 (p=0.010). In the subgroup of patients with IQR/median<0.21, classification A had the highest diagnostic accuracy with p=0.007 versus classification B (85.5%), and $p<10^{-3}$ versus others.

Management for antiviral therapy in clinical practice—Antiviral therapy was considered when FibroMeter classification was ≥F2/3, LSE: ≥F2, Fibrotest: ≥F2, classifications A and B: ≥F2±1, and classification C: ≥F2. By using classification A, 12.1% of patients in the validation set were considered for antiviral therapy whereas they had no/mild fibrosis at liver biopsy (Table 7 of Example 1). On the other hand, 9.7% of patients had no treatment whereas they had significant fibrosis at liver biopsy. Finally, classification A provided the highest rate of patients well managed for antiviral therapy (78.2%, p<0.040 versus others classifications).

TABLE 1 OF EXAMPLE 1

Patients characteristics at inclusion

| | All | Set Exploratory | Validation | p |
|---|---|---|---|---|
| Patients (n) | 729 | 349 | 380 | — |
| Male sex (%) | 61.3 | 60.2 | 62.4 | 0.531 |
| Age (years) | 51.7 ± 11.2 | 52.1 ± 11.2 | 51.3 ± 11.2 | 0.347 |
| Metavir F (%): | | | | $<10^{-3}$ |
| 0 | 4.0 | 1.4 | 6.3 | |
| 1 | 37.7 | 30.7 | 44.2 | |
| 2 | 25.8 | 35.5 | 16.8 | |
| 3 | 17.6 | 20.6 | 14.7 | |
| 4 | 15.0 | 11.7 | 17.9 | 0.020 |
| Significant fibrosis (%) | 58.3 | 67.9 | 49.5 | $<10^{-3}$ |
| Reliable biopsy (%) | 93.5 | 92.6 | 94.2 | 0.391 |
| LSE result (kPa) | 10.0 ± 7.9 | 9.9 ± 8.1 | 10.1 ± 7.7 | 0.755 |
| IQR/median <0.21 (%) | 66.9 | 66.2 | 67.6 | 0.700 |

LSE: liver stiffness evaluation; kPa: kilopascal; IQR: interquartile range

TABLE 2 OF EXAMPLE 1

Selection of candidate predictors at bootstrapped stepwise binary logistic regressions, as a function of diagnostic target

| Fibrosis tests | Significant fibrosis (Metavir F ≥ 2) | Severe fibrosis (Metavir F ≥ 3) | Cirrhosis (Metavir F = 4) |
|---|---|---|---|
| FibroMeter | 920 | 903 | 610 |
| FibroMeter F4 | — | — | 284 |
| Fibrotest | 113 | 173 | 88 |
| Hepascore | 216 | 74 | 172 |
| Fib4 | 85 | 103 | 62 |
| APRI | 350 | 504 | 59 |
| LSE | 964 | 1000 | 993 |

Stepwise binary logistic regressions were performed on 1000 bootstrap samples of 349 subjects from the exploratory set. The table depicts the number of times any fibrosis test was selected across the 1000 multivariate analyses. For each diagnostic target, LSE and FibroMeter were the mostly selected variables.

TABLE 3

AUROC of FibroMeter, LSE and their synchronous combination as a function of diagnostic target and patient group

| Diagnostic target | Fibrosis test | Set Exploratory | Validation | p | All |
|---|---|---|---|---|---|
| Metavir F ≥ 2 | FibroMeter | 0.806 ± 0.026 | 0.839 ± 0.022 | 0.333 | 0.813 ± 0.017 |
| | LSE | 0.785 ± 0.026 | 0.828 ± 0.022 | 0.207 | 0.791 ± 0.017 |
| | F ≥ 2-index | 0.835 ± 0.023 | 0.875 ± 0.019 | 0.180 | 0.846 ± 0.015 |
| | FibroMeter vs LSE | 0.513 | 0.685 | — | 0.301 |
| | FibroMeter vs F ≥ 2-index | 0.027 | 0.0020 | — | 0.0002 |
| | LSE vs F ≥ 2-index | 0.024 | 0.0086 | — | 0.0002 |
| Metavir F ≥ 3 | FibroMeter | 0.776 ± 0.025 | 0.880 ± 0.020 | 0.0012 | 0.829 ± 0.016 |
| | LSE | 0.816 ± 0.025 | 0.881 ± 0.019 | 0.038 | 0.847 ± 0.016 |
| | F ≥ 3-index | 0.830 ± 0.022 | 0.918 ± 0.017 | 0.0016 | 0.875 ± 0.014 |
| | FibroMeter vs LSE | 0.163 | 0.993 | — | 0.324 |
| | FibroMeter vs F ≥ 3-index | $<10^{-4}$ | 0.0002 | — | $<10^{-4}$ |
| | LSE vs F ≥ 3-index | 0.458 | 0.014 | — | 0.019 |
| Metavir F = 4 | FibroMeter | 0.814 ± 0.031 | 0.897 ± 0.021 | 0.027 | 0.861 ± 0.018 |
| | LSE | 0.878 ± 0.032 | 0.927 ± 0.017 | 0.176 | 0.905 ± 0.017 |
| | F4-index | 0.890 ± 0.028 | 0.947 ± 0.014 | 0.069 | 0.921 ± 0.015 |
| | FibroMeter vs LSE | 0.059 | 0.193 | — | 0.026 |
| | FibroMeter vs F4-index | 0.0004 | 0.0002 | — | $<10^{-4}$ |
| | LSE vs F4-index | 0.511 | 0.120 | — | 0.133 |

TABLE 4 OF EXAMPLE 1

Rate of patients included in the intervals of reliable diagnosis defined by the ≥90% negative (NPV) and positive (PPV) predictive values for significant fibrosis (Metavir F ≥ 2) and ≥95% predictive values for cirrhosis (Metavir F = 4), as a function of patient group and fibrosis test.

| Set | Fibrosis test | Metavir F ≥ 2 NPV ≥ 90% | PPV ≥ 90% | NPV + PPV ≥ 90% | Metavir F ≥ 3 NPV ≥ 90% | PPV ≥ 90% | NPV + PPV ≥ 90% | Metavir F = 4 NPV ≥ 95% | PPV ≥ 90% | PPV ≥ 95% | NPV + PPV ≥ 95% |
|---|---|---|---|---|---|---|---|---|---|---|---|
| Exploratory | FibroMeter | 3.2 (90.9) | 52.4 (89.6) | 55.6 (89.7) | 41.8 (89.7) | 0.0 (—) | 41.8 (89.7) | 65.9 (94.8) | 0.0 (—) | 0.0 (—) | 65.9 (94.8) |
| | Fibroscan | 1.1 (100.0) | 32.7 (90.4) | 33.8 (90.7) | 43.3 (90.1) | 3.2 (90.9) | 46.4 (90.1) | 86.0 (94.7) | 2.6 (88.9) | 1.4 (100.0) | 87.4 (94.8) |
| | F ≥ 2-index [a] | 9.2 (90.6) | 46.1 (90.1) | 55.3 (90.2) | 44.7 (89.7) | 5.2 (88.9) | 49.9 (89.7) | 87.7 (94.8) | 3.2 (90.9) | 2.0 (100.0) | 89.7 (94.9) |

TABLE 4 OF EXAMPLE 1-continued

Rate of patients included in the intervals of reliable diagnosis defined by the ≥90% negative (NPV) and positive (PPV) predictive values for significant fibrosis (Metavir F ≥ 2) and ≥95% predictive values for cirrhosis (Metavir F = 4), as a function of patient group and fibrosis test.

| Set | Fibrosis test | Metavir F ≥ 2 | | | Metavir F ≥ 3 | | | Metavir F = 4 | | | |
|---|---|---|---|---|---|---|---|---|---|---|---|
| | | NPV ≥ 90% | PPV ≥ 90% | NPV + PPV ≥ 90% | NPV ≥ 90% | PPV ≥ 90% | NPV + PPV ≥ 90% | NPV ≥ 95% | PPV ≥ 90% | PPV ≥ 95% | NPV + PPV ≥ 95% |
| Validation | FibroMeter | 1.2 (100.0) | 47.6 (72.0) | 48.8 (72.7) | 47.0 (94.2) | 0.0 (—) | 47.0 (94.2) | 64.2 (97.2) | 0.0 (—) | 0.0 (—) | 64.2 (97.2) |
| | Fibroscan | 0.9 (100.0) | 37.3 (76.4) | 38.2 (77.0) | 44.5 (93.2) | 2.1 (100.0) | 46.7 (93.5) | 83.3 (93.1) | 2.1 (100.0) | 1.8 (100.0) | 85.2 (93.2) |
| | F ≥ 3-index [a] | 7.6 (100.0) | 41.5 (82.5) | 49.1 (85.2) | 51.2 (95.3) | 7.3 (100.0) | 58.5 (95.9) | 85.2 (93.6) | 2.4 (100.0) | 2.1 (100.0) | 87.3 (93.8) |
| All | FibroMeter | 2.2 (93.3) | 50.1 (81.5) | 52.3 (82.0) | 44.3 (92.0) | 0.0 (—) | 44.3 (92.0) | 65.1 (93.9) | 0.0 (—) | 0.0 (—) | 65.1 (95.9) |
| | Fibroscan | 1.0 (100.0) | 34.9 (83.1) | 35.9 (83.6) | 43.9 (91.6) | 2.7 (94.4) | 46.5 (91.8) | 84.7 (93.9) | 2.4 (93.8) | 1.6 (700.0) | 86.3 (94.0) |
| | F4-index [a] | 8.4 (94.7) | 43.9 (86.6) | 52.3 (87.9) | 47.9 (92.6) | 6.2 (95.2) | 54.1 (92.9) | 86.5 (94.2) | 2.8 (94.7) | 2.1 (100.0) | 88.5 (94.3) |

Cut-offs for NPV ≥ 90% and PPV ≥ 90% were calculated in the exploratory set and tested in the validation set and the whole population.
Significant fibrosis. Cut-offs for NPV ≥ 90%: FibroMeter: ≤0.110, Fibroscan: ≤3.2, F ≥ 2-index: ≤0.248; cut-offs for PPV ≥ 90%: FibroMeter: ≥0.608, Fibroscan: ≥9.2, F ≥ 2-index: ≥0.784. Severe fibrosis. Cut-offs for NPV ≥ 90%: FibroMeter: ≤0.554, Fibroscan: ≤6.8, F ≥ 3-index: ≤0.220; cut-offs for PPV ≥ 90%: Fibroscan: ≥32.3, F ≥ 3-index: ≥0.870. Cirrhosis. Cut-offs for NPV ≥ 95%: FibroMeter: ≤0.757, Fibroscan: ≤14.5, F4-index: ≤0.244; cut-offs for PPV ≥ 90%: Fibroscan: ≥34.1, F4-index: ≥0.817; Cut-offs for PPV ≥ 95%: Fibroscan: ≥35.6, F4-index: ≥0.896.
[a] SF-index for significant fibrosis, X-index for severe fibrosis, and C-index for cirrhosis.

TABLE 5 OF EXAMPLE 1

Implementation of 3 new classifications for the non invasive diagnosis of fibrosis, derived from the interpretation of the interval of reliable diagnosis of several fibrosis tests (F ≥ 2- and F ≥ 3 indexes, F ≥ 3- and F ≥ 4 indexes, FibroMeter and Fibroscan).

| | | Reliable intervals of F ≥ 2-index | | | |
|---|---|---|---|---|---|
| | | F0/1 | F1/2 | F2 ± 1 | F ≥ 2 |
| Reliable intervals of F ≥ 3-index | F ≤ 2 | *F0/1* (29/32) | *F1/2* (55/61) | *F1/2* (50/63) | — |
| | F2 ± 1 | — | — | *F2 ± 1* (32/32) | *F2/3* (65/86) |
| | F ≥ 2 | — | — | — | *F ≥ 2* (54/57) |
| | F ≥ 3 | — | — | — | *F3/4* (16/18) |
| Reliable intervals of F4-index | F ≤ 3 | *F0/1* (29/32) | *F1/2* (55/61) | *F2 ± 1* (92/95) | *F2/3* (90/118) |
| | F ≥ 2 | — | — | — | *F ≥ 2* (35/36) |
| | F4 | — | — | — | *F4* (7/7) |
| Reliable intervals of LSE for F ≥ 3 | F ≤ 2 | *F0/1* (9/9) | *F1/2* (68/74) | *F1/2* (21/23) | *F2* (23/45) |
| | F2 ± 1 | *F1* 1/1 | *F1/2* (23/26) | *F2 ± 1* (8/9) | *F2/3* (43/48) |
| | F ≥ 2 | — | *F2* (4/13) | *F2/3* (6/9) | *F ≥ 2* (77/80) |
| | F ≥ 3 | — | — | — | *F ≥ 3* (10/10) |

The new classifications are depicted in italic (into brackets: rate of well classified patients in each class of the new classification according to liver biopsy results). Grey cells correspond to discordant results.

TABLE 6 OF EXAMPLE 1

Diagnostic accuracies (% of well classified patients) of several fibrosis tests classifications as a function of patient group

| | Set | | | |
|---|---|---|---|---|
| | Exploratory | Validation | p | All |
| Classification | | | | |
| Classification A | 86.2 | 84.2 | 0.516 | 85.3 |
| Classification B | 88.3 | 82.4 | 0.038 | 85.4 |
| Classification C | 84.0 | 70.3 | <10⁻³ | 77.3 |
| FibroMeter | 67.6 | 69.7 | 0.575 | 68.7 |
| Fibroscan [a] | 54.4 | 63.3 | 0.024 | 58.7 |
| Fibroscan [b] | 45.0 | 59.0 | <10⁻³ | 51.8 |
| Fibroscan [c] | 46.1 | 59.0 | 10⁻³ | 52.4 |
| Fibroscan [d] | 52.7 | 63.9 | 0.004 | 58.1 |
| Fibrotest | 33.5 | 43.9 | 0.005 | 38.8 |
| p | | | | |
| Classification A vs classification B | 0.143 | 0.146 | — | 1.000 |
| Classification A vs classification C | 0.229 | <10⁻³ | — | <10⁻³ |
| Classification A vs FibroMeter | <10⁻³ | <10⁻³ | — | <10⁻³ |
| Classification A vs Fibroscan [a] | <10⁻³ | <10⁻³ | — | <10⁻³ |
| Classification A vs Fibrotest | <10⁻³ | <10⁻³ | — | <10⁻³ |
| Classification B vs classification C | 0.032 | <10⁻³ | — | <10⁻³ |
| Classification B vs FibroMeter | <10⁻³ | <10⁻³ | — | <10⁻³ |
| Classification B vs Fibroscan [a] | <10⁻³ | <10⁻³ | — | <10⁻³ |
| Classification B vs Fibrotest | <10⁻³ | <10⁻³ | — | <10⁻³ |
| Classification C vs FibroMeter | <10⁻³ | 0.720 | — | <10⁻³ |
| Classification C vs Fibroscan [a] | <10⁻³ | 0.049 | — | <10⁻³ |
| Classification C vs Fibrotest | <10⁻³ | <10⁻³ | — | <10⁻³ |
| FibroMeter vs Fibroscan [a] | <10⁻³ | 0.029 | — | <10⁻³ |
| FibroMeter vs Fibrotest | <10⁻³ | <10⁻³ | — | <10⁻³ |
| Fibroscan [a] vs Fibrotest | <10⁻³ | <10⁻³ | — | <10⁻³ |

[a] 6 classes (de Ledinghen, GCB 2008);
[b] 4 classes (Ziol 2005),
[c] 4 classes (Stebbing 2009 + ≥9.6 kPa pour F ≥ 3),
[d] 3 classes (Stebbing 2009)

TABLE 7 OF EXAMPLE 1

Management of patient for antiviral therapy according to the results of fibrosis tests classifications (rates of patients in the validation population, %)

| Liver biopsy result Management according classification result [a] | Metavir F0/1 | | Metavir F ≥ 2 | | Well managed |
|---|---|---|---|---|---|
| | No treatment | Treatment | No treatment | Treatment | |
| Classification A | 41.5 | 12.1 | 9.7 | 36.7 | 78.2 |
| Classification B | 27.0 | 26.7 | 4.2 | 42.1 | 69.1 |
| Classification C | 33.9 | 19.7 | 7.3 | 39.1 | 73.0 |
| FibroMeter | 38.3 | 12.2 | 12.8 | 36.7 | 75.0 |
| Fibroscan (VDL) | 42.5 | 10.8 | 16.9 | 29.8 | 72.3 |
| Fibroscan (Ziol) | 42.5 | 10.8 | 16.9 | 29.8 | 72.3 |
| Fibroscan (Steb 4 cl) | 41.9 | 11.4 | 16.3 | 30.4 | 72.3 |
| Fibroscan (Steb 3 cl) | 41.9 | 11.4 | 16.3 | 30.4 | 72.3 |
| Fibrotest | 30.3 | 20.3 | 7.5 | 41.9 | 72.2 |

[a] Indication for antiviral therapy: Classifications A and B: ≥F2 ± 1; Classification C: ≥F2; FibroMeter: ≥F2/3; Fibroscan VDL: ≥F2; Fibroscan Ziol and Stebbing 4 classes: ≥F2; Fibroscan Stebbing 3cl: ≥F2/3; Fibrotest: ≥F2

Example 2

Patients 390 patients with chronic liver disease (CLD) hospitalized for a percutaneous liver biopsy at the University Hospitals of Angers and Bordeaux (France) were enrolled. 194 patients were included from April 2004 to June 2007 at the Angers site (group A, exploratory set), and 196 from September 2003 to April 2007 at the Bordeaux site (group B, validation set). Patients with the following cirrhosis complications were not included: ascites, variceal bleeding, systemic infection, and hepatocellular carcinoma. The non-invasive assessment of liver fibrosis by blood fibrosis tests and LSE was performed within one week prior to liver biopsy.

Methods

Histological Liver Fibrosis Assessment

Percutaneous liver biopsy was performed using Menghini's technique with a 1.4-1.6 mm diameter needle. In each site, liver fibrosis was evaluated by a senior pathologist specialized in hepatology according to Metavir staging (with a consensus reading in Angers). Significant fibrosis was defined by Metavir stages F≥2. Liver fibrosis evaluation was considered as reliable when biopsy length was ≥15 mm and/or portal tract number≥8 (17).

Fibrosis Blood Tests

The following blood tests were calculated according to published formulas or patents: APRI, FIB-4, Fibrotest, Hepascore, and FibroMeter (FM). Cause-specific formulas were used for FibroMeter (9, 18, 19). All blood assays were performed in the same laboratories of each site. The inter-laboratory reproducibility was excellent for these tests (20).

Liver Stiffness Evaluation

LSE (FibroScan®, EchoSens™, Paris, France) was performed by an experienced observer (>50 LSE before the study), blinded for patient data. LSE conditions were those recommended by the manufacturer, as detailed elsewhere (21, 22). LSE was stopped when 10 valid measurements were recorded. The LSE result was expressed in kPa and corresponded to the median of all valid measurements performed within the LSE. Inter-quartile range (kPa) was defined as previously described (21).

Statistical Analysis

Quantitative variables were expressed as mean±standard deviation, unless otherwise specified. When necessary, diagnostic cut-off values of fibrosis tests were calculated according to the highest Youden index (sensitivity+specificity−1). This technique allows maximizing the diagnostic accuracy with equilibrium between a high sensitivity and a high specificity by selecting an appropriate diagnostic cut-off. The diagnostic cut-off is here the values of blood test or LSE that distinguishes the patients as having or not the diagnostic target (significant fibrosis or cirrhosis).

Accuracy of fibrosis tests—The performance of fibrosis tests was mainly expressed as the area under the receiver operating characteristic curve (AUROC). The reliable individual diagnosis was determined either by the traditional negative (NPV) and positive (PPV) predictive values, or by the recently described method of reliable diagnosis intervals (18) (see Appendix for precise definitions). AUROCs were compared by the Delong test (23).

Synchronous combination of fibrosis tests—Combinations of blood tests and LSE were studied in 3 populations: group A, B, and A+B. In each population, we performed a forward binary logistic regression using significant fibrosis determined on liver biopsy as the dependent variable, and blood fibrosis tests and LSE results as independent variables. Then, by using the regression score provided by the multivariate analysis, we implemented a new fibrosis test for the diagnosis of significant fibrosis. The same methodology was used for the diagnosis of cirrhosis.

Sample size—Sample size was determined to show a significant difference for the diagnosis of significant fibrosis between FM and synchronous combination in the exploratory population. With α risk: 0.05, β risk: 0.20, significant fibrosis prevalence: 0.70, AUROC correlation: 0.70, and a bilateral test, the sample size was 159 patients for the following hypothesis of AUROC: FM: 0.84, synchronous combination: 0.90. The software programs used for statistical analyses were SPSS for Windows, version 11.5.1 (SPSS Inc., Chicago, Ill., USA) and SAS 9.1 (SAS Institute Inc., Cary, N.C., USA).

Results

Patients

The characteristics of the 390 patients are summarized in Table 1 of Example 2. Mean age of patients was 52.4 years, 67.9% were male, and 74.4% had significant fibrosis. 89.5% of patients had a liver biopsy considered as reliable. Liver Stiffness Evaluation failure occurred in 12 patients (overall failure rate: 3.1%). Among the 390 patients included, 332 had all 5 blood tests and LSE available.

TABLE 1 OF EXAMPLE 2

Patient characteristics at inclusion.

|  | All (n = 390) | A (n = 194) | B (n = 196) | p [a] |
|---|---|---|---|---|
| Age (years) | 52.4 ± 13.4 | 50.8 ± 12.7 | 53.9 ± 14.0 | 0.03 |
| Male sex (%) | 67.9 | 68.0 | 67.9 | 0.97 |
| Cause of liver disease (%) |  |  |  | <$10^{-3}$ |
| Virus | 48.7 | 54.1 | 43.4 |  |
| Alcohol | 27.2 | 26.3 | 28.1 |  |
| NAFLD | 4.9 | 9.8 | 0.0 |  |
| Other | 19.2 | 9.8 | 28.6 |  |
| Metavir fibrosis stage (%) |  |  |  | <$10^{-3}$ |
| F0 | 7.2 | 4.1 | 10.2 |  |
| F1 | 18.5 | 19.6 | 17.3 |  |
| F2 | 23.1 | 26.3 | 19.9 |  |
| F3 | 20.3 | 27.3 | 13.3 |  |
| F4 | 31.0 | 22.7 | 39.3 | <$10^{-3}$ |
| Significant fibrosis (%) | 74.4 | 76.3 | 72.4 | 0.39 |
| Reliable biopsy (%) | 89.5 | 95.3 | 82.6 | <$10^{-3}$ |
| IQR/LSE result <0.21 (%) | 59.4 | 58.5 | 60.3 | 0.73 |

IQR: interquartile range (kiloPascal)
[a] By t-test or $\chi^2$ between the groups A and B Diagnosis of Significant Fibrosis
Accuracy of Blood Tests and LSE (Table 2 of Example 2)

LSE AUROC was significantly higher than that of Hepascore, FIB-4, and APRI for the diagnosis of significant fibrosis, and was not significantly different from FibroMeter and Fibrotest AUROCs.

TABLE 2 OF EXAMPLE 2

AUROCs of blood tests and liver stiffness evaluation (LSE) as a function of diagnostic target, in the 332 patients having all 5 blood tests and LSE available.

|  | Significant fibrosis | Cirrhosis |
|---|---|---|
| AUROC: |  |  |
| FibroMeter (FM) | 0.836 | 0.834 |
| Fibrotest (FT) | 0.826 | 0.813 |
| Hepascore (HS) | 0.799 | 0.806 |
| FIB-4 | 0.787 | 0.793 |
| APRI | 0.762 | 0.691 |
| LSE | 0.858 | 0.915 |
| Comparison (p) [a]: |  |  |
| FM vs FT | 0.622 | 0.326 |
| FM vs HS | 0.074 | 0.101 |
| FM vs FIB-4 | 0.030 | 0.078 |
| FM vs APRI | 0.004 | <$10^{-3}$ |
| FM vs LSE | 0.417 | <$10^{-3}$ |
| FT vs HS | 0.195 | 0.786 |
| FT vs FIB-4 | 0.119 | 0.416 |
| FT vs APRI | 0.022 | <$10^{-3}$ |
| FT vs LSE | 0.257 | <$10^{-3}$ |
| HS vs FIB-4 | 0.700 | 0.663 |
| HS vs APRI | 0.264 | <$10^{-3}$ |
| HS vs LSE | 0.046 | <$10^{-3}$ |
| FIB-4 vs APRI | 0.302 | <$10^{-3}$ |
| FIB-4 vs LSE | 0.016 | <$10^{-3}$ |
| APRI vs LSE | 0.003 | <$10^{-3}$ |

[a] By Delong test

Synchronous Combination

Combination of non-invasive tests (Table 3 of Example 2)—In each of the three populations tested, significant fibrosis defined by liver biopsy was independently diagnosed by FibroMeter at the first step and Liver Stiffness Evaluation at the second step. The regression score provided by the binary logistic regression performed in group A (exploratory set) was: 3.6224.FM+0.4408.LSE result–3.9850. This score was used to implement a diagnostic synchronous combination of FibroMeter and Liver Stiffness Evaluation called significant fibrosis-index (SF-index). This new fibrosis test was then evaluated in the validation sets: group B (Bordeaux center) and the pooled group A+B.

TABLE 3 OF EXAMPLE 2

Fibrosis tests independently associated with significant fibrosis or cirrhosis defined by liver biopsy, as a function of patient group (A: Angers, B: Bordeaux).

| Patient Group | Significant fibrosis | | | Cirrhosis | | |
|---|---|---|---|---|---|---|
|  | Independent variables [a] | p | Diagnostic accuracy (%) [b] | Independent variables [a] | p | Diagnostic accuracy (%) [b] |
| A | 1. FibroMeter | <$10^{-3}$ | 82.0 | 1. LSE | <$10^{-3}$ | 89.7 |
|  | 2. LSE | <$10^{-3}$ | 87.6 | 2. FibroMeter | 0.031 | 88.7 |
| B | 1. FibroMeter | <$10^{-3}$ | 78.2 | 1. LSE | <$10^{-3}$ | 82.4 |
|  | 2. LSE | 0.012 | 80.3 | 2. FibroMeter | 0.017 | 83.0 |
| All | 1. FibroMeter | <$10^{-3}$ | 80.6 | 1. LSE | <$10^{-3}$ | 85.1 |
|  | 2. LSE | <$10^{-3}$ | 85.3 | 2. FibroMeter | $10^{-3}$ | 86.1 |

LSE: liver stiffness evaluation;
[a] Variables independently associated with significant fibrosis or cirrhosis with increasing order of step (the first step is the most accurate variable);
[b] Cumulative diagnostic accuracy for the second step Performance of SF-index (Table 4 of Example 2)—SF-index AUROCs were not significantly different between groups A and B. SF-index AUROC was significantly higher than that of FibroMeter (FM) or Liver Stiffness Evaluation (LSE) in the whole population. FIG. 1 shows that SF-index had the better performance profile: its misclassification rate was significantly lower than LSE in Metavir F≤1 stages and significantly lower than FM in Metavir F≥2 stages.

TABLE 4 OF EXAMPLE 2

AUROCs of synchronous combinations (FM + LSE index).

|  | Significant fibrosis | | | Cirrhosis | | |
|  | Patient group | | | | | |
|  | All | A | B | All | A | B |
| --- | --- | --- | --- | --- | --- | --- |
| AUROC: | | | | | | |
| FibroMeter | 0.834 | 0.839 | 0.843 | 0.835 | 0.822 | 0.839 |
| LSE | 0.867 | 0.889 | 0.850 | 0.923 | 0.931 | 0.922 |
| FM + LSE index [a] | 0.892 | 0.917 | 0.874 | 0.917 | 0.923 | 0.913 |
| Comparison (p) [b]: | | | | | | |
| FM vs LSE | 0.162 | 0.150 | 0.839 | <10⁻³ | 10⁻³ | 0.004 |
| FM vs FM + LSE index | <10⁻³ | <10⁻³ | 0.210 | <10⁻³ | <10⁻³ | <10⁻³ |
| LSE vs FM + LSE index | 0.011 | 0.081 | 0.042 | 0.458 | 0.463 | 0.445 |

Comparison with those of FibroMeter (FM) and liver stiffness evaluation (LSE), as a function of diagnostic target and patient group (A: Angers, B: Bordeaux).
[a] SF-index for significant fibrosis, C-index for cirrhosis
[b] By Delong test As shown on Table 4 of Example 2, SF-index inherited of the lowest misclassification rate provided by each single test in each fibrosis stage: the blood test in F0/1 stages, and LSE in F≥2 stages (see also FIG. 1).

Discordances between LSE and FM—Discordances between fibrosis tests for the diagnostic target were calculated according to the diagnostic cut-off determined by the highest Youden index. FM and LSE were concordant in 279 (73.0%) patients of whom 88.9% were correctly classified according to liver biopsy (F≤1: 77.0%, F≥2: 94.3%). FM and LSE were discordant in the 103 (27.0%) remaining patients of whom 68 (66.0%) were correctly classified by SF-index according to liver biopsy results (Table 5 of Example 2). Finally, SF-index correctly classified 316 (82.7%) patients and improved correct classification (i.e., discordances between FM and LSE resolved by SF-index) in 33 (8.6%) patients.

Moreover, the SF-index resolved 66% of discordant cases between the blood test and LSE (Table 5 of Example 2).

TABLE 5 OF EXAMPLE 2

Discordances.

| Classification by fibrosis tests [a] | | Impact of FM + LSE index on classification | Patients (n) according to diagnostic target studied | |
| --- | --- | --- | --- | --- |
| FM + LSE index [b] | FM and LSE [c] | by FM and LSE | F ≥ 2 | F4 |
| Correct | Both incorrect | Favorable | 0 | 0 |
|  | Discordant |  | 68 | 54 |
|  | Both correct | Neutral | 248 | 275 |
| Incorrect | Both incorrect |  | 31 | 28 |
|  | Discordant | Unfavorable | 35 | 25 |
|  | Both correct |  | 0 | 0 |
|  |  | Net improvement | 33 [d] (8.6%) | 29 [e] (7.6%) |

Impact of FM + LSE index on discordances between FibroMeter (FM) and liver stiffness evaluation (LSE) for the diagnosis of significant fibrosis or cirrhosis in the whole population.
[a] Respective diagnostic cut-off values used for significant fibrosis or cirrhosis, according to the highest Youden index: FM: 0.538 and 0.873; LSE: 6.9 and 13.0 kiloPascals; FM + LSE index: 0.753 (SF-index) and 0.216 (C-index)
[b] Classification by SF-index for significant fibrosis or C-index for cirrhosis expressed as correct or incorrect according to liver biopsy.
[c] Classification of both tests based on liver biopsy. "Discordant" means than one test is correct and the other one is incorrect.
[d] Favorable (68) – unfavorable (35) effect = improvement (33)
[e] Favorable (54) – unfavorable (25) effect = improvement (29)

Methods Reliably Classifying 100% of Patients

New sequential algorithm—SF-index included significantly more patients than FM or LSE in the classical intervals of ≥90% predictive values (see Appendix for precise definition), especially in the ≤90% NPV interval (Table 6 of Example 2). By using SF-index with ≥90% predictive values in 81.7% of patients and liver biopsy required in the remaining 18.3% of patients, a correct diagnosis of significant fibrosis based on liver biopsy was obtained in 91.9% of patients (Table 6 of Example 2). This two-step sequential algorithm was called Angers SF-algorithm (FIG. 2).

Reliable diagnosis intervals of SF-index—With this recently described method (18), accuracy is made ≥90% in the interval(s) between the previous intervals of 90% predictive values by changing the diagnostic target. The interest is to offer a reliable diagnosis for all patients. In the indeterminate interval determined by the ≥90% predictive values of SF-index, the proportion of Metavir fibrosis stages was F0: 20.0%, F1: 40.0%, and F2: 32.9% according to LIVER BIOPSY (FIG. 3a). Thus, it was possible to obtain three intervals of reliable diagnosis: F0/1 in the ≤90% NPV interval, F1±1 in the intermediate interval (correct classification: 92.9%), and F≥2 (F3±1) in the ≥90% PPV interval. Finally, this new classification correctly classified 90.6% of patients with 0% of liver biopsy.

Comparison of algorithms (Table 7 of Example 2)—We compared the Angers SF-algorithm to those previously published in Bordeaux (24) and in Padova (16). The population tested was the 332 patients having Fibrotest, FibroMeter, APRI, and LSE available. The Padova algorithm had significantly higher accuracy (95.2%) compared to other algorithms due to a significantly higher rate of required LB. The Angers algorithm had a significantly lower rate of required liver biopsy compared to other algorithms. Thus, Angers SF-algorithm had the best compromise between high correct classification and low liver biopsy requirement, reflected by a much lower liver biopsy/accuracy ratio.

Diagnosis of Cirrhosis

Accuracy of Blood Tests and LSE (Table 2 of Example 2)

LSE had a significantly higher AUROC than the blood tests for the diagnosis of cirrhosis.

Synchronous Combination

Combination of non-invasive tests (Table 3 of Example 2)—The most accurate combination of fibrosis tests for the diagnosis of cirrhosis was LSE+FM. The regression score provided by the binary logistic regression performed in the group A (exploratory set) was: 0.1162.LSE result+ 1.9714.FM−4.6616. This score was used to implement a diagnostic synchronous combination of LSE and FM called cirrhosis-index (C-index). This new fibrosis test was then evaluated in the validation sets: group B (Bordeaux center) and the pooled group A+B.

Performance of C-index (Table 4 of Example 2)—C-index AUROCs were not significantly different between groups A and B. In each group tested, C-index had a significantly higher AUROC than FM, but the difference with the LSE AUROC was not significant.

Discordances between LSE and FM—FM and LSE were concordant in 303 (79.3%) patients of whom 90.8% were correctly classified according to LIVER BIOPSY (F≤3: 94.7%, F4: 82.1%). FM and LSE were discordant in the 79 (20.7%) remaining patients of whom 54 (68.4%) were correctly classified by C-index according to LIVER BIOPSY results (Table 5 of Example 2). Finally, C-index correctly classified 329 (86.1%) patients and improved correct classification (i.e., discordances between FM and LSE resolved by C-index) in 29 (7.6%) patients.

Methods Reliably Classifying 100% of Patients

New sequential algorithm (Table 6 of Example 2)—The C-index included significantly more patients than FM or LSE in the classical intervals of ≥90% predictive values. By using C-index with ≥90% predictive values in 90.6% of patients and liver biopsy required in the remaining 9.4% of patients, a correct diagnosis of cirrhosis based on liver biopsy was obtained in 91.1% of patients (Table 6 of Example 2). This two-step sequential algorithm was called Angers C-algorithm (FIG. 4).

Reliable diagnosis intervals of C-index—In the indeterminate interval determined by the ≥90% predictive values of C-index, the proportion of Metavir fibrosis stages was F2: 11.1%, F3: 22.2%, and F4: 58.3% according to liver (FIG. 3b). Thus, it was possible to obtain three intervals of reliable diagnosis: no cirrhosis (F≤3) in the ≤90% NPV interval, F≥2 (F3±1) in the intermediate interval (correct classification: 91.6%), and cirrhosis (F4) in the ≥90% PPV interval. Finally, this new classification correctly classified 90.3% of patients with 0% of liver biopsy.

TABLE 6 OF EXAMPLE 2

New sequential algorithm. Rates of patients included and correctly classified by fibrosis tests in the intervals of ≥90% predictive values for the diagnosis of significant fibrosis or cirrhosis in the whole population, as a function of fibrosis test.

| Diagnostic target | Fibrosis test | Rate (%) of patients included in the intervals defined by 90% predictive values | | | Accuracy (%) | |
|---|---|---|---|---|---|---|
| | | ≥90% NPV | Indeterminate [a] | ≥90% PPV | Fibrosis test [b] | Algorithm [c] |
| Significant fibrosis (F ≥ 2) | FibroMeter | 0.3 | 36.4 | 63.4 | 57.3 | 93.7 |
| | LSE | 0.5 | 28.8 | 70.7 | 64.1 | 92.9 |
| | SF-index | 8.1 | 18.3 | 73.6 | 73.6 | 91.9 |
| Cirrhosis (F4) | FibroMeter | 44.2 | 42.1 | 13.6 | 52.1 | 94.2 |
| | LSE | 68.3 | 12.6 | 19.1 | 78.8 | 91.4 |
| | C-index | 70.4 | 9.4 | 20.2 | 81.7 | 91.1 |

[a] Proportion of patients for whom diagnosis remains uncertain (NPV and PPV < 90%), thus requiring a liver biopsy. Comparison of patient rates by McNemar test. Significant fibrosis: LSE vs FibroMeter: p = 0.006, SF-index vs FibroMeter or LSE: p < 10⁻³; cirrhosis: FibroMeter vs C-index or LSE: p < 10⁻³, C-index vs LSE: p = 0.02.
[b] Rate of patients correctly classified by the intervals of ≥90% (negative and positive) predictive values, among the whole population. Comparison of patient rates by McNemar test. Significant fibrosis: LSE vs FibroMeter: p = 0.005, SF-index vs FibroMeter or LSE: p < 10⁻³; cirrhosis: FibroMeter vs C-index or LSE: p < 10⁻³, C-index vs LSE: p = 0.007.
[c] Algorithm is defined by a two-step procedure: the fibrosis test is initially used with the interval of ≥90% predictive values, and a liver biopsy is subsequently required for patients included in the interval of indeterminate diagnosis. Thus, algorithm accuracy is calculated as the sum of patients correctly classified by the fibrosis test in the whole population (4$^{th}$ result column) and liver biopsy requirement (2$^{nd}$ result column) where accuracy is 100% by definition. Comparison of rates by McNemar test between FibroMeter and C-index for cirrhosis: p = 0.04, others: p: NS.

Comparison of sequential algorithms (Table 7 of Example 2)—The Bordeaux algorithm had significantly higher accuracy for cirrhosis compared to other algorithms. However, Angers C-algorithm had a significantly lower rate of required liver biopsy compared to other algorithms. Thus, as for significant fibrosis, Angers C-algorithm had the best compromise between high correct classification and low liver biopsy requirement, reflected by a much lower liver biopsy/accuracy ratio.

TABLE 7 OF EXAMPLE 2

Comparison of accuracies and liver biopsy (LB) requirements between sequential algorithms of Angers (present study), Bordeaux (24), and Padova (16), for the diagnosis of significant fibrosis or cirrhosis.

| Diagnostic target | Algorithm | Blood test accuracy (%) [a] | LB (%) [b] | Algorithm accuracy (%) | | | LB/accuracy ratio [d] |
|---|---|---|---|---|---|---|---|
| | | | | All causes [c] | Virus | Other | |
| Significant fibrosis | Angers SF | 89.8 | 20.2 | 91.9 | 92.2 | 91.5 | 0.22 |
| | Bordeaux | 86.5 | 28.6 | 90.4 | 88.8 | 92.2 | 0.33 |
| | Padova | 91.1 | 46.1 | 95.2 | 95.0 | 95.4 | 0.51 |

TABLE 7 OF EXAMPLE 2-continued

Comparison of accuracies and liver biopsy (LB) requirements between sequential algorithms of Angers (present study), Bordeaux (24), and Padova (16), for the diagnosis of significant fibrosis or cirrhosis.

| Diagnostic target | Algorithm | Blood test accuracy (%) [a] | LB (%) [b] | Algorithm accuracy (%) All causes [c] | Virus | Other | LB/accuracy ratio [d] |
|---|---|---|---|---|---|---|---|
| Cirrhosis | Angers C | 90.0 | 9.3 | 91.0 | 93.9 | 87.6 | 0.10 |
| | Bordeaux | 92.3 | 25.3 | 94.3 | 94.4 | 94.1 | 0.27 |
| | Padova | 81.1 | 20.5 | 84.9 | 86.0 | 83.7 | 0.25 |

Population tested is the 332 patients having FibroMeter, Fibrotest, APRI and LSE available together. Grey cells indicate the most important results.
[a] Accuracy (%) of blood tests included in patients without liver biopsy whose proportion can be deduced from the following column. Paired comparison was not possible.
[b] Rate (%) of liver biopsy required by the algorithm. Comparison of rates by McNemar test. Significant fibrosis: Angers vs Bordeaux: $p = 0.02$, Padova vs Angers or Bordeaux: $p < 10^{-3}$; cirrhosis: Angers vs Bordeaux or Padova: $p < 10^{-3}$; Bordeaux vs Padova: $p = 0.129$.
[c] Comparison of patient rates by McNemar test. Significant fibrosis: Padova vs Angers: $p = 0.02$, or Bordeaux: $p = 0.007$; Angers vs Bordeaux: $p = 0.50$; cirrhosis: Bordeaux vs Angers: $p = 0.04$, or Padova: $p < 10^{-3}$; Angers vs Padova: $p = 0.007$.
[d] Ratio: rate of required liver biopsy ($2^{nd}$ result column)/blood test accuracy ($1^{st}$ result column).

REFERENCES

1. Oberti F, Valsesia E, Pilette C, Rousselet M C, Bedossa P, Aube C, et al. Noninvasive diagnosis of hepatic fibrosis or cirrhosis. Gastroenterology 1997; 113:1609-1616.
2. Croquet V, Vuillemin E, Ternisien C, Pilette C, Oberti F, Gallois Y, et al. Prothrombin index is an indirect marker of severe liver fibrosis. Eur J Gastroenterol Hepatol 2002; 14:1133-1141.
3. Afdhal N H, Nunes D. Evaluation of liver fibrosis: a concise review. Am J Gastroenterol 2004; 99:1160-1174.
4. Sebastiani G, Alberti A. Non invasive fibrosis biomarkers reduce but not substitute the need for liver biopsy. World J Gastroenterol 2006; 12:3682-3694.
5. Wai C T, Greenson J K, Fontana R J, Kalbfleisch J D, Marrero J A, Conjeevaram H S, et al. A simple noninvasive index can predict both significant fibrosis and cirrhosis in patients with chronic hepatitis C. Hepatology 2003; 38:518-526.
6. Sterling R K, Lissen E, Clumeck N, Sola R, Correa M C, Montaner J, et al. Development of a simple noninvasive index to predict significant fibrosis in patients with HIV/HCV coinfection. Hepatology 2006; 43:1317-1325.
7. Imbert-Bismut F, Ratziu V, Pieroni L, Charlotte F, Benhamou Y, Poynard T. Biochemical markers of liver fibrosis in patients with hepatitis C virus infection: a prospective study. Lancet 2001; 357:1069-1075.
8. Rosenberg W M, Voelker M, Thiel R, Becka M, Burt A, Schuppan D, et al. Serum markers detect the presence of liver fibrosis: a cohort study. Gastroenterology 2004; 127:1704-1713.
9. Cales P, Oberti F, Michalak S, Hubert-Fouchard I, Rousselet M C, Konate A, et al. A novel panel of blood markers to assess the degree of liver fibrosis. Hepatology 2005; 42:1373-1381.
10. Patel K, Gordon S C, Jacobson I, Hezode C, Oh E, Smith K M, et al. Evaluation of a panel of non-invasive serum markers to differentiate mild from moderate-to-advanced liver fibrosis in chronic hepatitis C patients. J Hepatol 2004; 41:935-942.
11. Adams L A, Bulsara M, Rossi E, DeBoer B, Speers D, George J, et al. Hepascore: an accurate validated predictor of liver fibrosis in chronic hepatitis C infection. Clin Chem 2005; 51:1867-1873.
12. Sandrin L, Fourquet B, Hasquenoph J M, Yon S, Fournier C, Mal F, et al. Transient elastography: a new noninvasive method for assessment of hepatic fibrosis. Ultrasound Med Biol 2003; 29:1705-1713.
13. Bourliere M, Penaranda G, Ouzan D, Renou C, Botta-Fridlund D, Tran A, et al. Optimized stepwise combination algorithms of non-invasive liver fibrosis scores including Hepascore in hepatitis C virus patients. Aliment Pharmacol Ther 2008; 28:458-467.
14. Bourliere M, Penaranda G, Renou C, Botta-Fridlund D, Tran A, Portal I, et al. Validation and comparison of indexes for fibrosis and cirrhosis prediction in chronic hepatitis C patients: proposal for a pragmatic approach classification without liver biopsy. J Viral Hepat 2006; 13:659-670.
15. Sebastiani G, Vario A, Guido M, Alberti A. Sequential algorithms combining non-invasive markers and biopsy for the assessment of liver fibrosis in chronic hepatitis B. World J Gastroenterol 2007; 13:525-531.
16. Sebastiani G, Vario A, Guido M, Noventa F, Plebani M, Pistis R, et al. Stepwise combination algorithms of non-invasive markers to diagnose significant fibrosis in chronic hepatitis C. J Hepatol 2006; 44:686-693.
17. Nousbaum J B, Cadranel J F, Bonnemaison G, Bourliere M, Chiche L, Chor H, et al. Clinical practice guidelines on the use of liver biopsy. Gastroenterol Clin Biol 2002; 26:848-878.
18. Cales P, De Ledinghen V, Halfon P, Bacq Y, Leroy V, Boursier J, et al. Evaluating accuracy and increasing the reliable diagnosis rate of blood tests for liver fibrosis in chronic hepatitis C. Liver Int 2008; 28:1352-1362.
19. Cales P, Laine F, Boursier J, Deugnier Y, Moal V, Oberti F, et al. Comparison of blood tests for liver fibrosis specific or not to NAFLD. J Hepatol 2009; 50:165-173.
20. Cales P, Veillon P, Konate A, Mathieu E, Ternisien C, Chevailler A, et al. Reproducibility of blood tests of liver fibrosis in clinical practice. Clin Biochem 2008; 41:10-18.
21. Boursier J, Konate A, Gorea G, Reaud S, Quemener E, Oberti F, et al. Reproducibility of liver stiffness measurement by ultrasonographic elastometry. Clin Gastroenterol Hepatol 2008; 6:1263-1269.
22. Boursier J, Konate A, Guilluy M, Gorea G, Sawadogo A, Quemener E, et al. Learning curve and interobserver reproducibility evaluation of liver stiffness measurement by transient elastography. Eur J Gastroenterol Hepatol 2008; 20:693-701.
23. DeLong E R, DeLong D M, Clarke-Pearson D L. Comparing the areas under two or more correlated receiver operating characteristic curves: a nonparametric approach. Biometrics 1988; 44:837-845.
24. Castera L, Vergniol J, Foucher J, Le Bail B, Chanteloup E, Haaser M, et al. Prospective comparison of transient elastography, Fibrotest, APRI, and liver biopsy for the assessment of fibrosis in chronic hepatitis C. Gastroenterology 2005; 128:343-350.
25. Lucidarme D, Foucher J, Le Bail B, Vergniol J, Castera L, Duburque C, et al. Factors of Accuracy of Transient Elastography (Fibroscan) for the Diagnosis of Liver Fibrosis in Chronic Hepatitis C. Hepatology 2009; in press.
26. Bossuyt P M, Reitsma J B, Bruns D E, Gatsonis C A, Glasziou P P, Irwig L M, et al. The STARD statement for reporting studies of diagnostic accuracy: explanation and elaboration. Clin Chem 2003; 49:7-18.
27. Halfon P, Bacq Y, De Muret A, Penaranda G, Bourliere M, Ouzan D, et al. Comparison of test performance profile for blood tests of liver fibrosis in chronic hepatitis C. J Hepatol 2007; 46:395-402.
28. Boursier J, Bacq Y, Halfon P, Leroy V, De Ledinghen V, De Muret A, et al. Improved diagnostic accuracy of blood tests for severe fibrosis and cirrhosis in chronic hepatitis C. Eur J Gastroenterol Hepatol 2009; 21:28-38.
29. Castera L. Use of elastometry (FibroScan) for the non-invasive staging of liver fibrosis. Gastroenterol Clin Biol 2007; 31:524-530.
30. Fraquelli M, Rigamonti C, Casazza G, Conte D, Donato M F, Ronchi G, et al. Reproducibility of transient elastography in the evaluation of liver fibrosis in patients with chronic liver disease. Gut 2007; 56:968-973.
31. Friedrich-Rust M, Ong M F, Martens S, Sarrazin C, Bojunga J, Zeuzem S, et al. Performance of transient elastography for the staging of liver fibrosis: a meta-analysis. Gastroenterology 2008; 134:960-974.
32. Cales P, Boursier J, Rousselet M C, Michalak S, Oberti F, Gallois Y, et al. Comparison of reproducibility of histology, blood tests and Fibroscan for liver fibrosis. Hepatology 2007; 46:834A.
33. Cales P, Boursier J, De Ledinghen V, Halfon P, Bacq Y, Leroy V, et al. Evaluation and improvement of a reliable diagnosis of cirrhosis by blood tests. Gastroenterol Clin Biol 2008; 32:1050-1060.
34. Castera L, Sebastiani G, Le Bail B, De Ledinghen V, Couzigou P, Alberti A. Prospective comparison of two algorithms combining non invasive tests for staging of liver fibrosis in chronic hepatitis C. Hepatology 2007; 46:320A.
35. Sebastiani G, Halfon P, Castera L, Mangia A, Di Marco V, Pirisi M, et al. Large-scale multicenter comparison of three algorithms combining serum non-invasive markers for liver fibrosis in chronic hepatitis C. J Hepatol 2008; 48:S282.
36. Poynard T, Halfon P, Castera L, Munteanu M, Imbert-Bismut F, Ratziu V, et al. Standardization of ROC curve areas for diagnostic evaluation of liver fibrosis markers based on prevalences of fibrosis stages. Clin Chem 2007; 53:1615-1622.
37. Lambert J, Halfon P, Penaranda G, Bedossa P, Cacoub P, Carrat F. How to measure the diagnostic accuracy of noninvasive liver fibrosis indices: the area under the ROC curve revisited. Clin Chem 2008; 54:1372-1378.
38. Obuchowski N A. An ROC-type measure of diagnostic accuracy when the gold standard is continuous-scale. Stat Med 2006; 25:481-493.

The invention claimed is:

1. A microprocessor comprising a computer algorithm to perform a method of diagnosing the presence and/or severity of a liver pathology and/or of monitoring the effectiveness of a curative treatment against a liver pathology in an individual comprising:
obtaining a blood test score of at least one blood test from an individual, wherein the blood test comprises obtaining a blood sample from the individual and analyzing a marker for liver pathology in the blood sample to obtain a score;
obtaining a result of using at least one measuring device to practice a non-invasive physical method for diagnosing liver fibrosis, wherein the physical method is further defined as comprising medical imaging and/or clinical measurement and is further defined as elastometry; and
performing a mathematical function to combine the blood test score with the result of the physical method for diagnosing liver function to obtain a second score useful for the diagnosis of the presence and/or severity of a liver pathology and/or of monitoring the effectiveness of a curative treatment against a liver pathology in the individual.

2. The microprocessor of claim 1, wherein the blood test is further defined as an Hepascore, Fibrotest™, FibroMeter, Elf score, or Fibrospect blood test.

3. The microprocessor of claim 1, wherein the liver disease or condition is significant porto-septal fibrosis, severe porto-septal fibrosis, centrolobular fibrosis, cirrhosis, or persinusoidal fibrosis and of alcoholic or non-alcoholic origin.

4. The microprocessor of claim 1, wherein the mathematical function is a logistic regression.

5. The microprocessor of claim 1, wherein the mathematical function is a binary logistic regression.

6. The microprocessor of claim 1, wherein the individual is a patient with chronic Hepatitis C.

7. The microprocessor of claim 1, wherein performing a mathematical function to combine the blood test score with the result of the physical method for diagnosing liver function to obtain a second score is done at least twice to obtain at least two second scores, and the at least two second scores are then combined in an algorithm based on diagnostically reliable intervals.

8. The microprocessor of claim 1, wherein the method further comprises treating the individual for a liver pathology.

9. The microprocessor of claim 1, wherein elastometry is further defined as selected from the group consisting of Fibroscan, Acoustic Radiation Force Impulse imaging (ARFI imaging), supersonic elastometry, transient elastography (TE) and MRI stiffness.

* * * * *